US007235351B2

(12) United States Patent
Fukusaka et al.

(10) Patent No.: US 7,235,351 B2
(45) Date of Patent: Jun. 26, 2007

(54) SQUALIRIUM COMPOUND, THERMALLY DEVELOPABLE PHOTOGRAPHIC MATERIAL CONTAINING SAID COMPOUND, AND IMAGE FORMING METHOD THEREOF

(76) Inventors: Kiyoshi Fukusaka, c/o Konica Minolta Technology Center, Inc., 2970 Ishikawa-machi, Hachioji-shi, Tokyo (JP) 192-8505; Osamu Ishige, c/o Konica Minolta Technology Center, Inc., 2970 Ishikawa-machi, Hachioji-shi, Tokyo (JP) 192-8505; Rie Sakuragi, c/o Konica Minolta Technology Center, Inc., 2970 Ishikawa-machi, Hachioji-shi, Tokyo (JP) 192-8505

( * ) Notice: Subject to any disclaimer, the term of this patent is extended or adjusted under 35 U.S.C. 154(b) by 0 days.

(21) Appl. No.: 11/396,832

(22) Filed: Apr. 3, 2006

(65) Prior Publication Data

US 2006/0228656 A1 Oct. 12, 2006

(30) Foreign Application Priority Data

Apr. 12, 2005 (JP) ............................ 2005-114293

(51) Int. Cl.

*G03C 1/498* (2006.01)
*G03C 1/40* (2006.01)
*G03C 1/83* (2006.01)
*C07D 315/00* (2006.01)

(52) U.S. Cl. ...................... 430/353; 430/617; 430/619; 430/944; 430/522; 549/415

(58) Field of Classification Search ................ 430/353, 430/522, 617, 619, 944; 549/415
See application file for complete search history.

(56) References Cited

U.S. PATENT DOCUMENTS 6,444,415 B1 * 9/2002 Tanaka et al. .............. 430/517
6,482,950 B1 * 11/2002 Garcia et al. ................. 546/66
7,138,224 B2 * 11/2006 Fukusaka et al. ........... 430/617

* cited by examiner

*Primary Examiner*—Richard L. Schilling
(74) *Attorney, Agent, or Firm*—Lucas & Mercanti, LLP

(57) ABSTRACT

A thermally developable photographic material containing a support, provided thereon: (i) a photosensitive layer containing photosensitive silver halide particles, and (ii) a layer containing at least one represented by formula below on one or both surfaces of the support

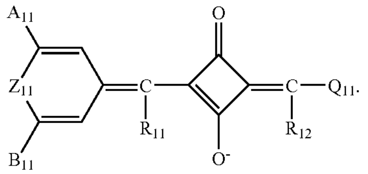

8 Claims, No Drawings

SQUALIRIUM COMPOUND, THERMALLY DEVELOPABLE PHOTOGRAPHIC MATERIAL CONTAINING SAID COMPOUND, AND IMAGE FORMING METHOD THEREOF

This application is based on Japanese Patent Application No. 2005-114293 filed on Apr. 12, 2005, in Japanese Patent Office, the entire content of which is hereby incorporated by reference.

FIELD OF THE INVENTION

The present invention relates to a new squalirium compound, and particularly to a thermally developable photographic material containing said compound, and an image forming method thereof.

BACKGROUND OF THE INVENTION

Dye is utilized in fields such as a colorant for a polymer material and dichroic dye for liquid crystal, in addition to fields such as an electrophotographic light-sensitive material of an electrophotographic printer, a recording material for an optical disk, a non-linear optical material and a material for a near-infrared cut filter. Dye utilized in these fields, specifically infrared dye, shows low stability against light or heat, and is desired to be further improved.

On the other hand, in the fields of medical diagnosis and graphic arts, antihalation (AH) dye and antiirradiation (AI) dye have been commonly utilized to maintain sharpness despite reflection and refraction of incident light at the time of exposure. Specifically, characteristics required for AH dye and AI dye, utilized in a thermally developable photographic material, include absorption of a desired wavelength of light, no adverse influence to silver halide emulsion, and no residual contamination on the material after development. However, few infrared dyes, which provide maximum absorption in the near-infrared region, and specifically in the region of 700–900 nm, and with very low absorption in the visible region, are known, and an example disclosed includes squalirium dye (for example, refer to Patent Literature 1 and 2). When dye described in these sourses is utilized in a thermally developable photographic material, stability during high heat storage of the photosensitive material is unacceptable, and further improvement has been demanded.

[Patent Literature 1] JP-A 58-220143 (hereinafter, JP-A refers to Japanese Patent Publication Open to Public Inspection)

[Patent Literature 2] U.S. Pat. No. 6,482,950

SUMMARY OF THE INVENTION

An object of this invention is to overcome the above-described drawbacks of the former patents and to provide a thermally developable photographic material exhibiting superior storage stability at high temperature and high humidity.

The above object of this invention can be achieved via the following constitutions.

Item 1. A thermally developable photographic material comprising a support, provided thereon:

(i) a photosensitive layer containing photosensitive silver halide particles, and (ii) a layer containing at least one represented by Formula (1) on one or both surfaces of the support.

Formula (1)

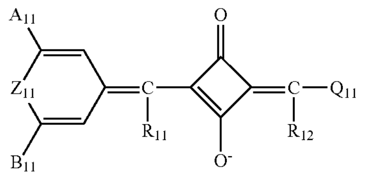

In above Formula (1), $R_{11}$ and $R_{12}$ are independently a hydrogen atom or a substituent, $Z_{11}$ is O, S, N—$R_1$, Se or Te, wherein $R_1$ is an alkyl group or an aryl group, $Q_{11}$ is a 6-membered heterocyclic ring, while $A_{11}$ and $B_{11}$ are both an aryl group, and either $A_{11}$ or $B_{11}$ is a substituted aryl group.

Item 2. The thermally developable photographic material of above Item 1, wherein the compound represented by Formula (1) is further represented by Formula (2).

Formula (2)

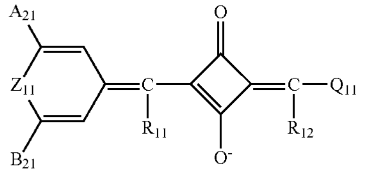

In above Formula (2), $R_{11}$, $R_{12}$, $Z_{11}$ and $Q_{11}$ are identical to $R_{11}$, $R_{12}$, $Z_{11}$ and $Q_{11}$ of Formula (1), $A_{21}$ and $B_{21}$ are also an aryl group, however $A_{21}$ and $B_{21}$ must not be the same aryl group.

Item 3. The thermally developable photographic material of Item 1, wherein the compound represented by Formula (1) is further represented by Formula (3).

Formula (3)

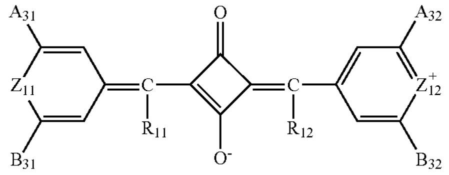

In above Formula (3), $R_{11}$, $R_{12}$ and $Z_{11}$ are identical to $R_{11}$, $R_{12}$ and $Z_{11}$ of Formula (1), $A_{31}$ and $B_{31}$ are also an aryl group, wherein at least either $A_{31}$ or $B_{31}$ is a substituted aryl group, $A_{32}$ and $B_{32}$ are also an aryl group, wherein at least either $A_{32}$ or $B_{32}$ is also a substituted aryl group, $Z_{12}$ is O, S, N—$R_2$, Se or Te, and $R_2$ is an alkyl or aryl group.

Item 4. The thermally developable photographic material of Item 1 or 2, wherein the compound represented by Formula (3) is further represented by following Formula (4).

Formula (4)

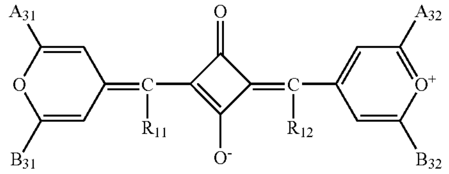

In above Formula (4), $R_{11}$ and $R_{12}$ are identical to $R_{11}$ and $R_{12}$ of Formula (1), also $A_{31}$, $B_{31}$, $A_{32}$ and $B_{32}$ are identical to $A_{31}$, $B_{31}$, $A_{32}$ and $B_{32}$ of Formula (3).

Item 5. The thermally developable photographic material of Item 1 or 2, wherein the compound represented by Formula (2) is further represented by following Formula (5).

Formula (5)

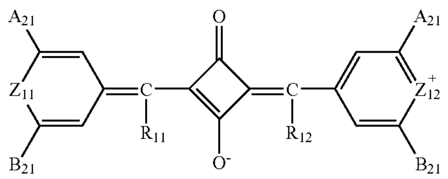

In above Formula (5), $R_{11}$, $R_{12}$ and $Z_{11}$ are identical to $R_{11}$, $R_{12}$, and $Z_{11}$ of Formula (1), $Z_{12}$ is identical to $Z_{12}$ of Formula (3), and $A_{21}$ and $B_{21}$ are the same as $A_{21}$ and $B_{21}$ of Formula (2).

Item 6. The thermally developable photographic material of any one of Items 1–5, wherein the compound represented by Formulas (4) and (5) is further represented by following Formula (6).

Formula (6)

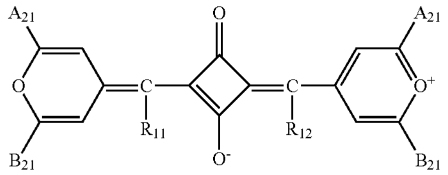

In above Formula (6), $R_{11}$ and $R_{12}$ are identical to $R_{11}$ and $R_{12}$ of Formula (1), and $A_{21}$ and $B_{21}$ are identical to $A_{21}$, and $B_{21}$ of Formula (2).

Item 7. An image forming method comprising the steps of:

(1) exposing the thermally developable photographic material of any one of Items 1–6 employing a laser light source; and (2) thermally developing the exposed thermally developable photographic material at a temperature of 80–150° C.

Item 8. A squalirium compound represented by Formula (6).

Formula (6)

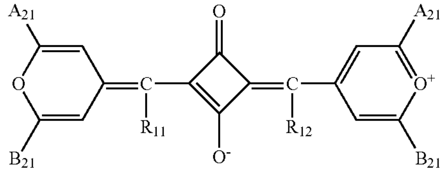

In above Formula (6), $R_{11}$ and $R_{12}$ are identical to $R_{11}$ and $R_{12}$ of Formula (1), and $A_{21}$ and $B_{21}$ are identical to $A_{21}$ and $B_{21}$ of Formula (2).

According to this invention, a thermally developable photographic material exhibiting superior storage stability can be realized. In particular, produced can be a thermally developable photographic material exhibiting superior sharpness in storage at high temperature and high humidity.

PREFERRED EMBODIMENTS OF THE INVENTION

It should be understood that no single element of any of the embodiments described herein is essential, and that it is within the contemplation of the invention that one or more elements (or method steps) of one or more embodiments of the invention as described herein may be omitted or their functionality may be combined with that of other elements as a general matter of design choice.

This invention will now be detailed.

In above-described Formula (1), $R_{11}$ and $R_{12}$ is each independently a hydrogen atom or a substituent. A substituent represented by $R_{11}$ and $R_{12}$ includes such as an alkyl group, a cycloalkyl group, an alkenyl group, an alkynyl group, an aryl group, a heterocyclic group, a halogen atom and a cyano group. Among these, preferable is a hydrogen atom, an alkyl group or an aryl group, but more preferable is a hydrogen atom or an alkyl group.

$Z_{11}$ is O, S, N—$R_1$, Se or Te, wherein $R_1$ is an alkyl group or an aryl group. $Z_{11}$ is preferably O, S or N—$R_1$ but more preferable is O or S.

$Q_{11}$ is a 6-membered heterocyclic ring, and the heterocyclic ring includes such as pyrylium, thiopyrylium, selenopyrylium, telluropyrylium, pyridinium, benzpyrylium, benzthiopyrylium and benzselenopyrylium, but preferably pyrylium, thiopyrylium or selenopyrylium, and more preferably pyrylium or thiopyrylium. These heterocyclic rings may be provided with a substituent. The substituent may include an alkyl group, a cycloalkyl group, a halogenated alkyl group, an alkenyl group, an alkynyl group, an aryl group, a heterocyclic group, a halogen group, a cyano group, a hydroxyl group, a carboxyl group, an alkoxy group, an aryloxy group, a silyloxy group, a heterocyclic oxy group, an acyloxy group, a carbamoyl group, an alkoxycarbonyloxy group, an aryloxycarbonyloxy group, an amino group, an aniline group, an acylamino group, an aminocarbonyl group, an alkoxycarbonylamino group, an aryloxycarbonylamino group, a sulfamoylamino group, an alkyl- and an aryl-sulfamoylamino group, a mercapto group, an alkylthio group, an arylthio group, a heterocyclic-thio group, a sulfamoyl group, a sulfo group, an alkyl- and an aryl-sulfinyl group, an alkyl- and an aryl-sulfonyl group, an acyl group, an aryloxycarbonyl group, an alkoxycarbonyl group, a carbamoyl group, an aryl- and a heterocyclic-azo group, an imido group, a silyl group, a hydrazine group, an ureido group, a borate group, a phosphite group, a sulfite group, as well as other substituents well known in the art.

$A_{11}$ and $B_{11}$ are an aryl group. These aryl groups may be provided with a substituent, which includes an alkyl group, a cycloalkyl group, a halogenated alkyl group, an alkenyl group, an alkynyl group, an aryl group, a heterocyclic group, a halogen group, a cyano group, a hydroxyl group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an anilino group, an acylamino group, an aminocarbonylamino group, an alkoxycarbonylamino group, an aryloxycarbonylamino group, a sulfamoylamino group, an alkyl- and an aryl-sulfamoylamino group, a mercapto group, an alkylthio group, an arylthio group, a heterocyclic-thio group, a sulfamoyl group, a sulfo group, an alkyl- and an aryl-sulfinyl group, an alkyl and an aryl-sulfonyl group, an acyl group, an aryloxycarbonyl group, an alkoxycarbonyl group, a carbamoyl group, an aryl- and a heterocyclic-azo group, an imido group, a silyl group, a hydrazino group, a ureido group, a borate group, a phosphate group, a sulfite group, as well as other substituents well known in the art. Preferable are an alkyl group, a cycloalkyl group, a halogenated alkyl group, an aryl group, a heterocyclic group, a halogen atom, a cyano group, an alkoxy group and an aryloxy group, but more preferable are an alkyl group, an aryl group, a halogen atom and an alkoxy group. Herein, at least either $A_{11}$ or $B_{11}$ is a substituted aryl group.

In Formula (2), $R_{11}$, $R_{12}$, $Z_{11}$ and $Q_{11}$ are identical to $R_{11}$, $R_{12}$, $Z_{11}$ and $Q_{11}$ in aforesaid Formula (1).

$A_{21}$ and $B_{21}$ are an aryl group. These aryl groups may be provided with a substituent, which include an alkyl group, a cycloalkyl group, a halogenated alkyl group, an alkenyl group, an alkynyl group, an aryl group, a heterocyclic group, a halogen group, a cyano group, a hydroxyl group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an anilino group, an acylamino group, an aminocarbonylamino group, an alkoxycarbonylamino group, an aryloxycarbonylamino group, a sulfamoylamino group, an alkyl- and an aryl-sulfamoylamino group, a mercapto group, an alkylthio group, an arylthio group, a heterocyclic-thio group, a sulfamoyl group, a sulfo group, an alkyl- and an aryl-sulfinyl group, an alkyl and an aryl-sulfonyl group, an acyl group, an aryloxycarbonyl group, an alkoxycarbonyl group, a carbamoyl group, an aryl- and a heterocyclic-azo group, an imido group, a silyl group, a hydrazino group, a ureido group, a borate group, a phosphite group, a sulfite group, as well as other substituents well known in the art. Preferable are an alkyl group, a cycloalkyl group, a halogenated alkyl group, an aryl group, a heterocyclic group, a halogen atom, a cyano group, an alkoxy group and an aryloxy group, but more preferable are an alkyl group, an aryl group, a halogen atom and an alkoxy group. Herein, $A_{21}$ and $B_{21}$ may never be the same aryl group.

In Formula (3), $R_{11}$, $R_{12}$, and $Z_{11}$ are identical to $R_{11}$, $R_{12}$ and $Z_{11}$ in aforesaid Formula (1).

$A_{31}$ and $B_{31}$ represent an aryl group. These aryl groups may be provided with a substituent, which include an alkyl group, a cycloalkyl group, a halogenated alkyl group, an alkenyl group, an alkynyl group, an aryl group, a heterocyclic group, a halogen group, a cyano group, a hydroxyl group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an anilino group, an acylamino group, an aminocarbonylamino group, an alkoxycarbonylamino group, an aryloxycarbonylamino group, a sulfamoylamino group, an alkyl- and an aryl-sulfamoylamino group, a mercapto group, an alkylthio group, an arylthio group, a heterocyclic-thio group, a sulfamoyl group, a sulfo group, an alkyl- and an aryl-sulfinyl group, an alkyl and an aryl-sulfonyl group, an acyl group, an aryloxycarbonyl group, an alkoxycarbonyl group, a carbamoyl group, an aryl- and a heterocyclic-azo group, an imido group, a silyl group, a hydrazino group, an ureido group, a borate group, a phosphite group, a sulfite group, as well as other substituents well known in the art. Preferable are an alkyl group, a cycloalkyl group, a halogenated alkyl group, an aryl group, a heterocyclic group, a halogen atom, a cyano group, an alkoxy group and an aryloxy group, but more preferable are an alkyl group, an aryl group, a halogen atom and an alkoxy group. Herein, at least either $A_{31}$ or $B_{31}$ is a substituted aryl group.

$A_{32}$ and $B_{32}$ are an aryl group. These aryl groups may be provided with a substituent, which include an alkyl group, a cycloalkyl group, a halogenated alkyl group, an alkenyl group, an alkynyl group, an aryl group, a heterocyclic group, a halogen group, a cyano group, a hydroxyl group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an anilino group, an acylamino group, an aminocarbonylamino group, an alkoxycarbonylamino group, an aryloxycarbonylamino group, a sulfamoylamino group, an alkyl- and an aryl-sulfamoylamino group, a mercapto group, an alkylthio group, an arylthio group, a heterocyclic-thio group, a sulfamoyl group, a sulfo group, an alkyl- and an aryl-sulfinyl group, an alkyl and an aryl-sulfonyl group, an acyl group, an aryloxycarbonyl group, an alkoxycarbonyl group, a carbamoyl group, an aryl- and a heterocyclic-azo group, an imido group, a silyl group, a hydrazino group, a ureido group, a borate group, a phosphite group, a sulfite group, as well as other substituents well known in the art. Preferable are an alkyl group, a cycloalkyl group, a halogenated alkyl group, an aryl group, a heterocyclic group, a halogen atom, a cyano group, an alkoxy group and an aryloxy group, but more preferable are an alkyl group, an aryl group, a halogen atom and an alkoxy group. Herein, at least either $A_{32}$ or $B_{32}$ is a substituted aryl group.

$Z_{12}$ is O, S, N—$R_2$, Se or Te, and $R_2$ is an alkyl group or an aryl group, while $Z_{12}$ is preferably O, S, or N—$R_2$, but more preferably O or S.

In Formula (4), $R_{11}$ and $R_{12}$ are identical to $R_{11}$ and $R_{12}$ in aforesaid Formula (1). $A_{31}$, $B_{31}$, $A_{32}$ and $B_{32}$ are identical to $A_{31}$, $B_{31}$, $A_{32}$ and $B_{32}$ in aforesaid Formula (3).

In Formula (5), $R_{11}$, $R_{12}$ and $Z_{11}$ are identical to $R_{11}$, $R_{12}$, and $Z_{11}$ in aforesaid Formula (1). $Z_{12}$ is identical to $Z_{12}$ in aforesaid Formula (3). $A_{21}$ and $B_{21}$ are identical to $A_{21}$ and $B_{21}$ in aforesaid Formula (2). In Formula (6), $R_{11}$ and $R_{12}$ are identical to $R_{11}$ and $R_{12}$ in aforesaid Formula (1). $A_{21}$ and $B_{21}$ are identical to $A_{21}$ and $B_{21}$ in aforesaid Formula (2).

In the following, specific examples of compounds represented by Formulas (1)-(6) will be shown, however, this invention is not limited thereto.

sq-1

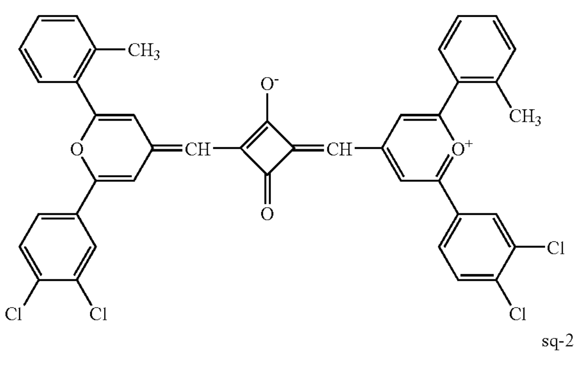

sq-2

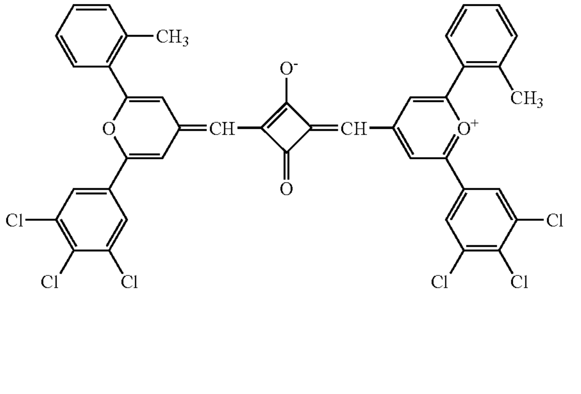

-continued
sq-3
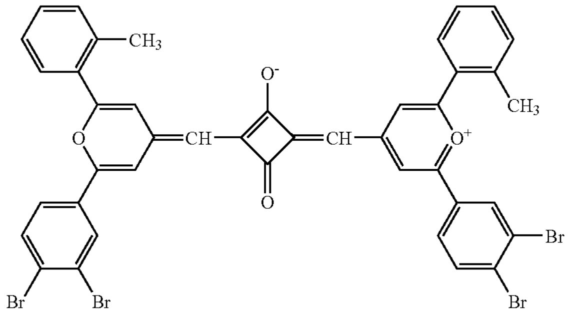
sq-4
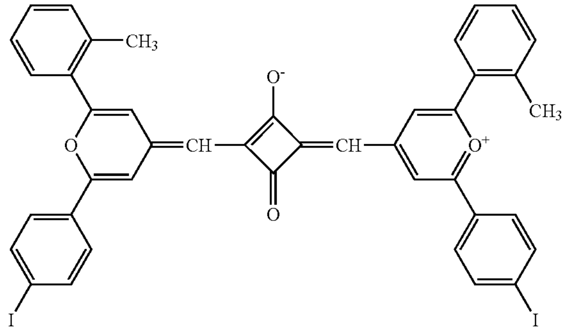
sq-5
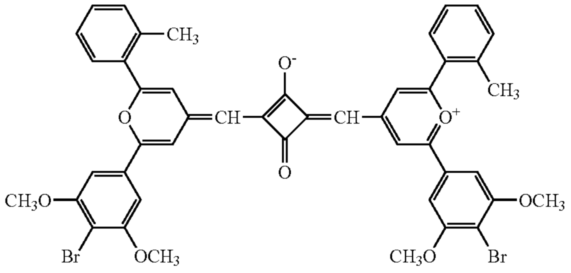
sq-6
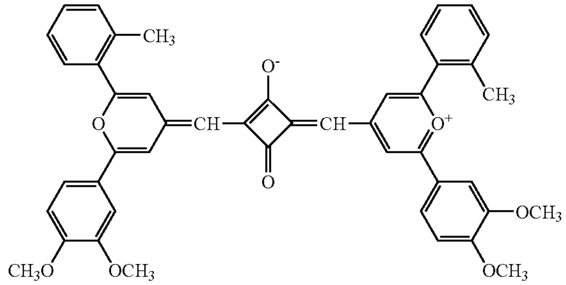
sq-7
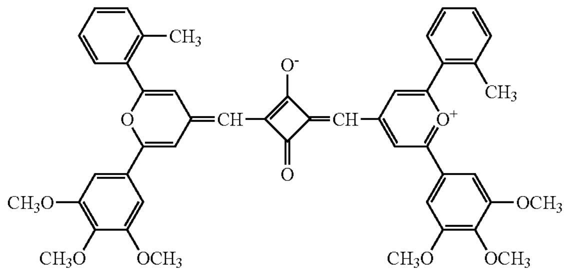
-continued
sq-8
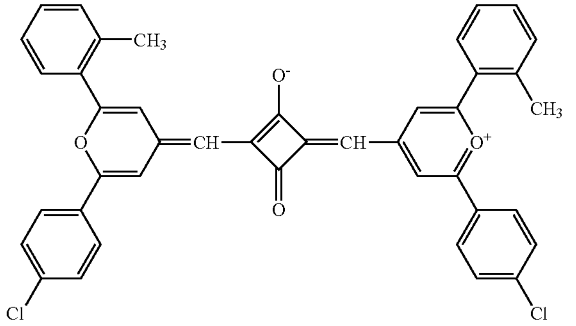
sq-9
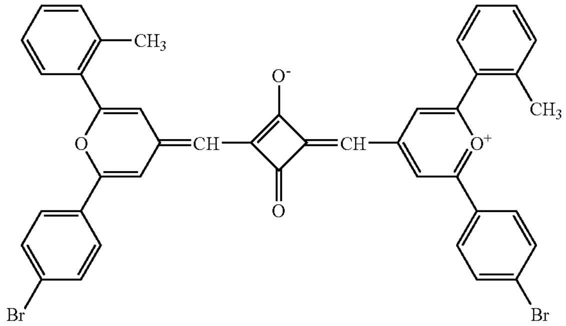
sq-10
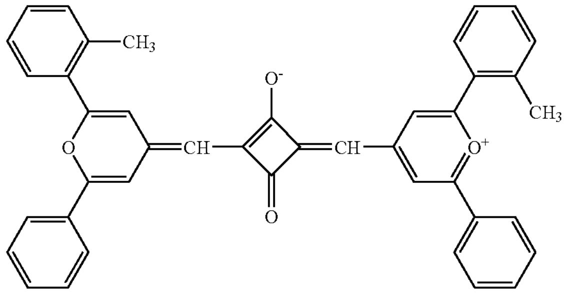
sq-11
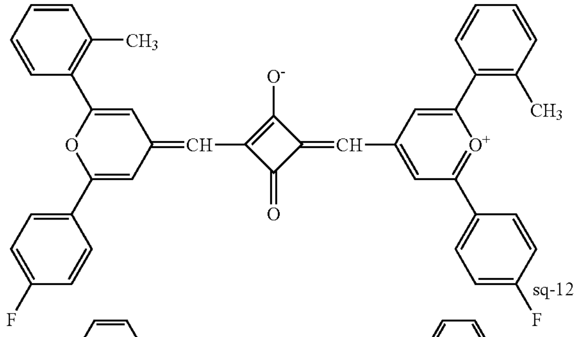
sq-12
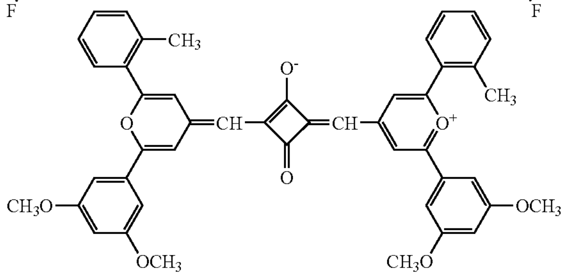

-continued
sq-13
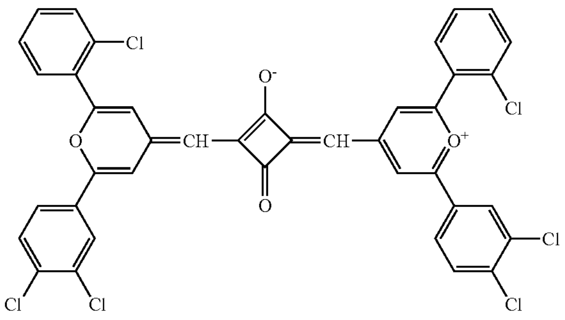
sq-14
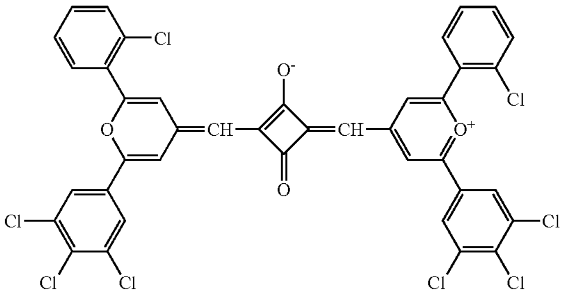
sq-15
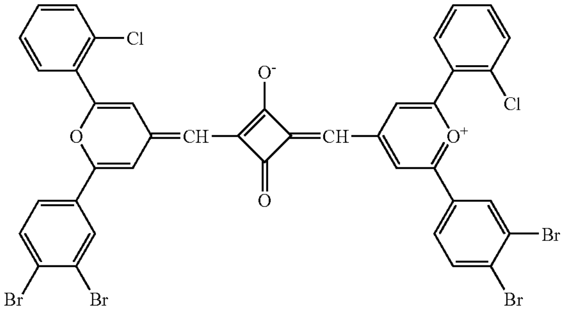
sq-16
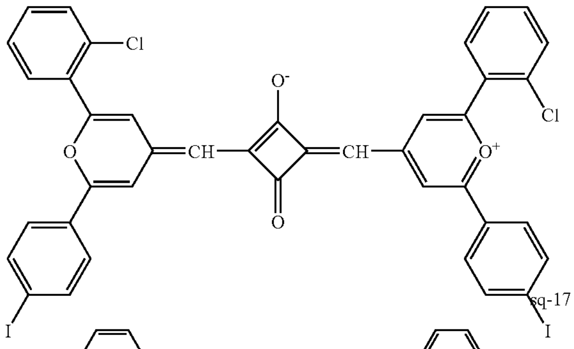
sq-17
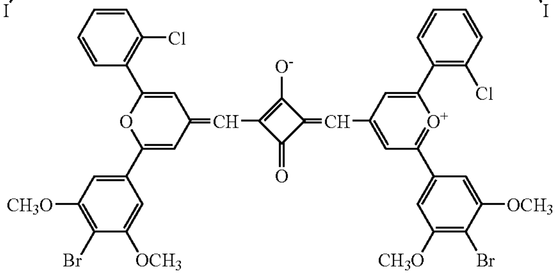
-continued
sq-18
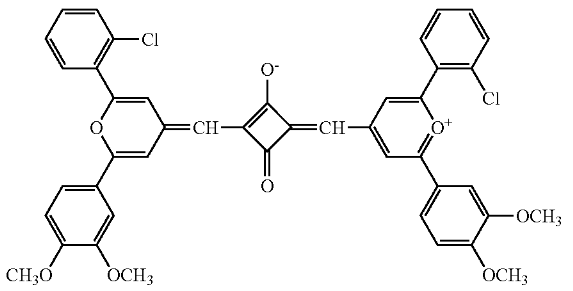
sq-19
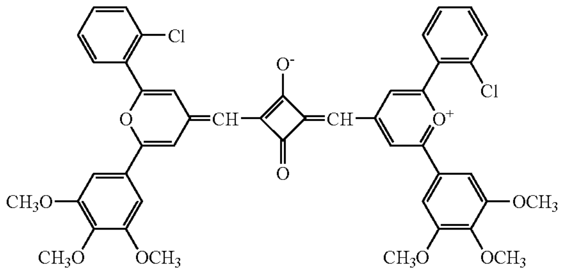
sq-20
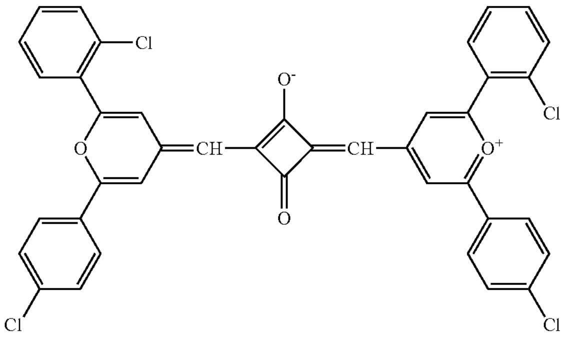
sq-21
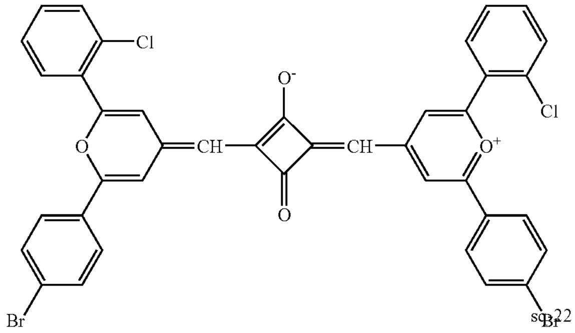
sq-22
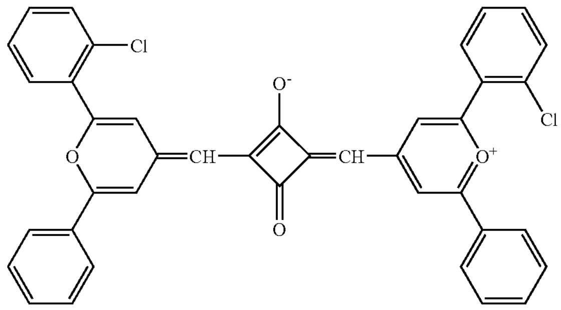

-continued
sq-23
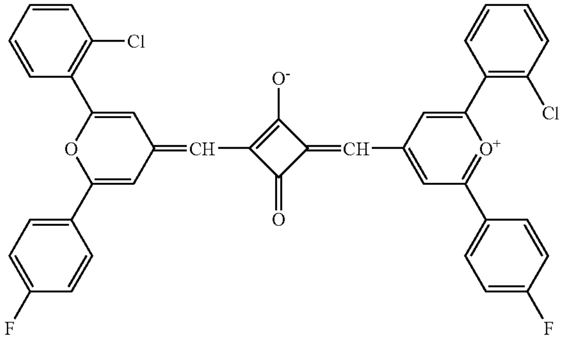
sq-24
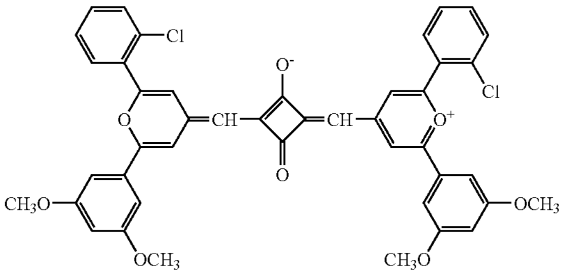
sq-25
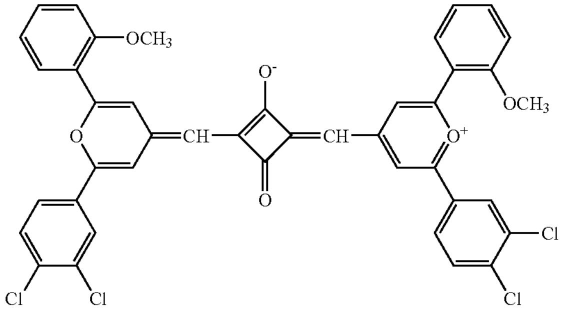
sq-26
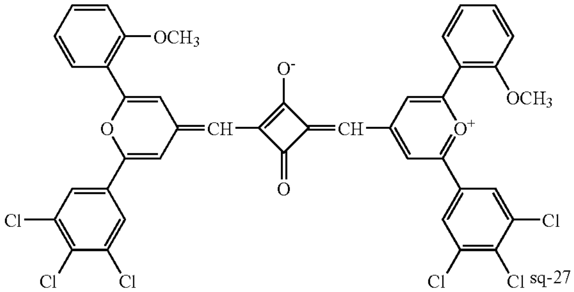
sq-27
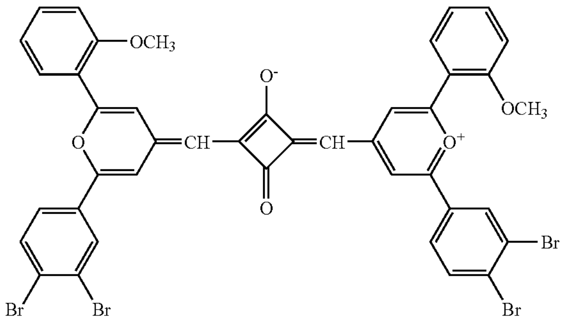
-continued
sq-28
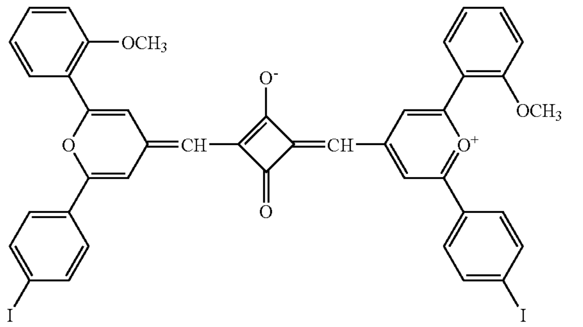
sq-29
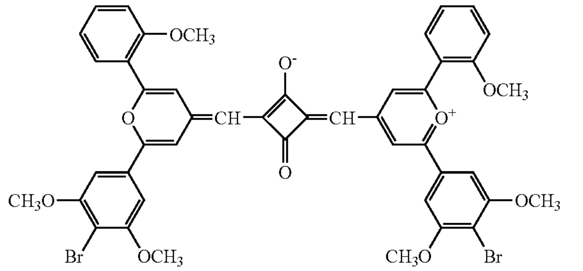
sq-30
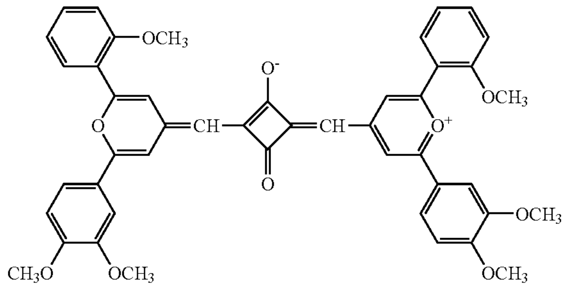
sq-31
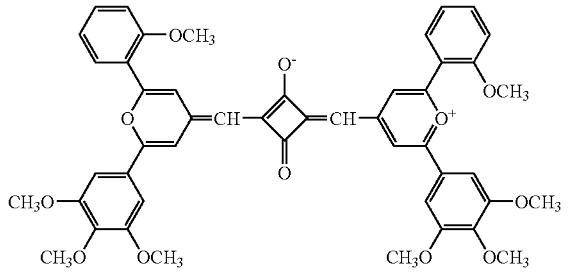
sq-32
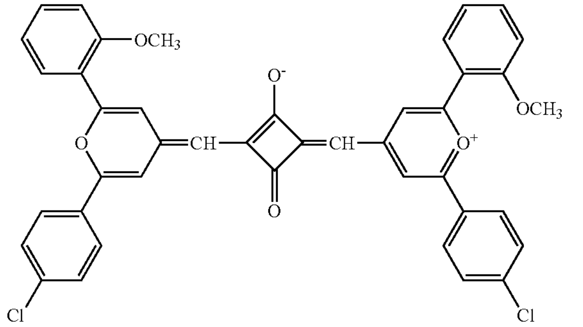

-continued
sq-33
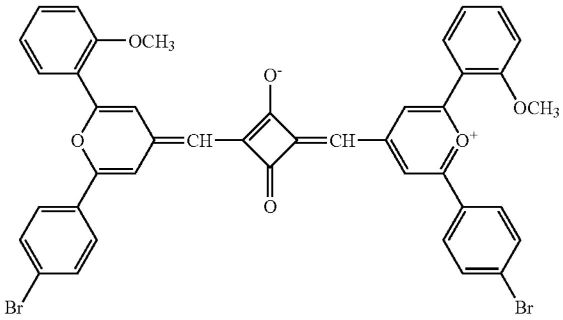
sq-34
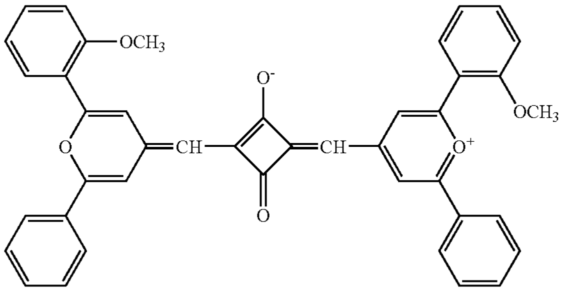
sq-35
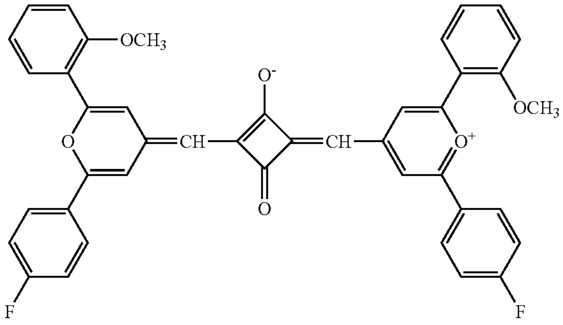
sq-36
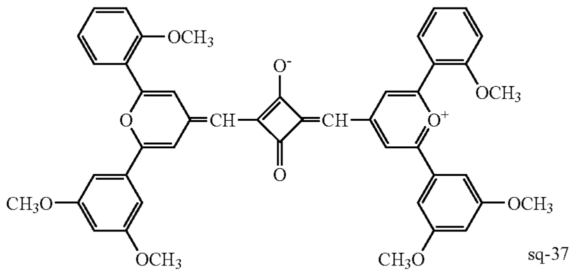
sq-37
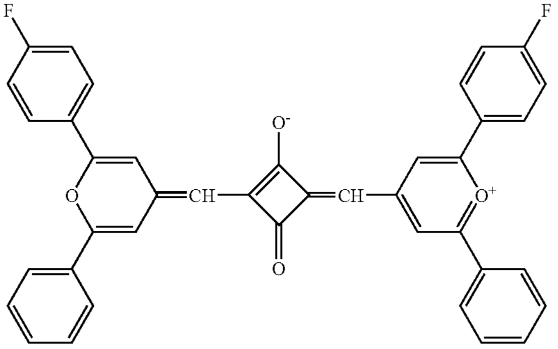
-continued
sq-38
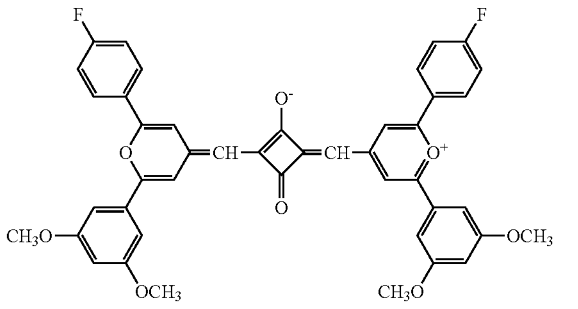
sq-39
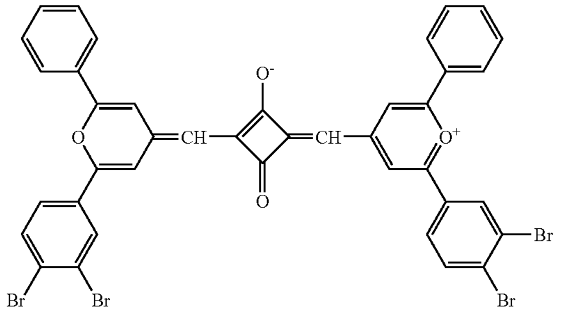
sq-40
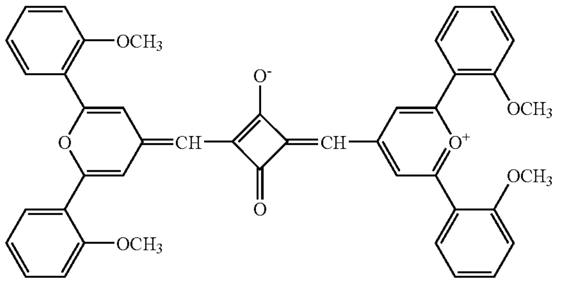
sq-41
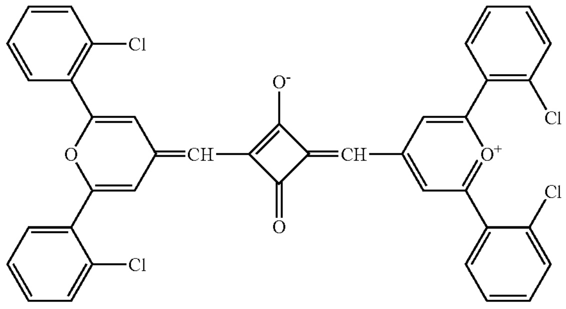
sq-42
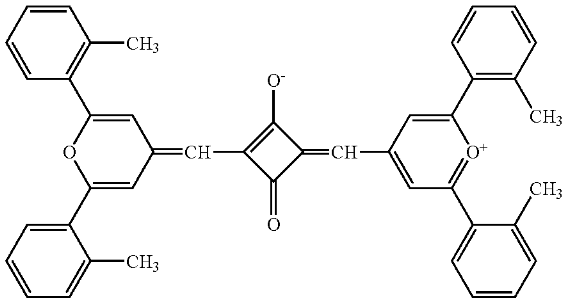

-continued
sq-43
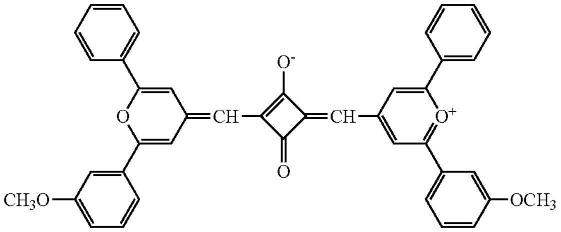
sq-44
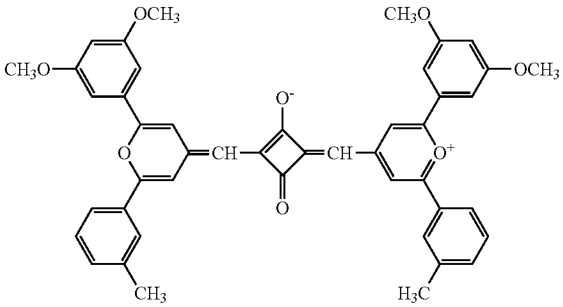
sq-45
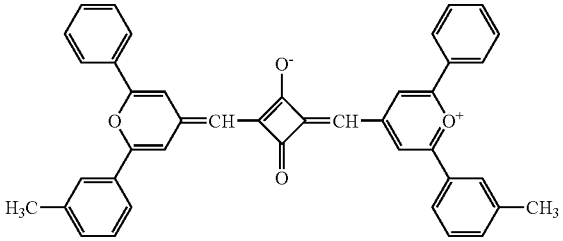
sq-46
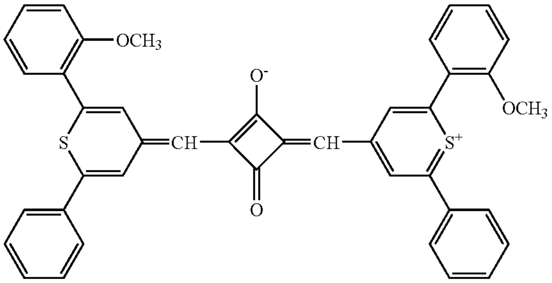
sq-47
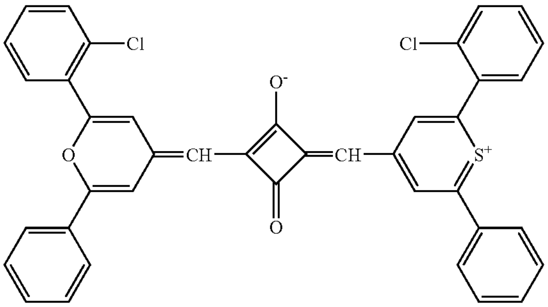
-continued
sq-48
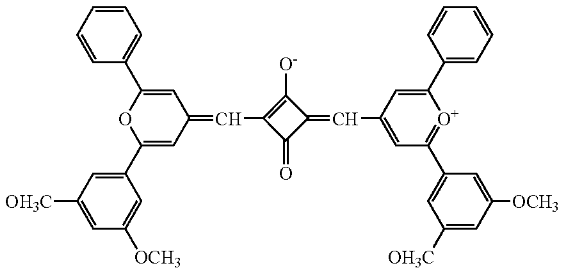
sq-49
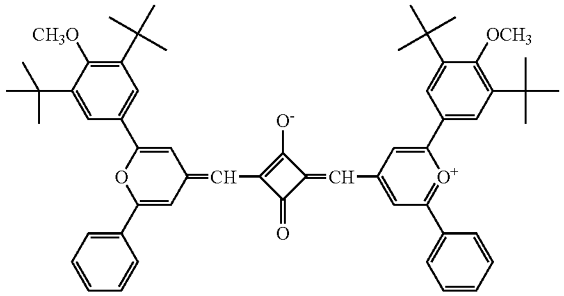
sq-50
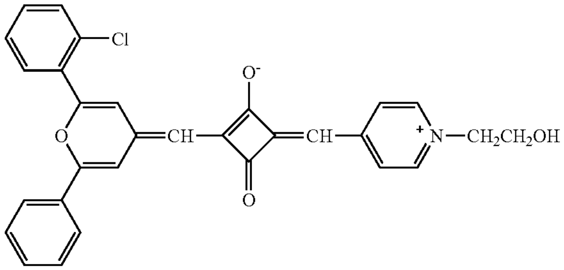
sq-51
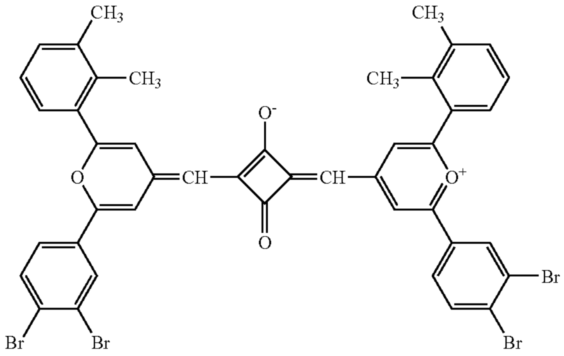
sq-52
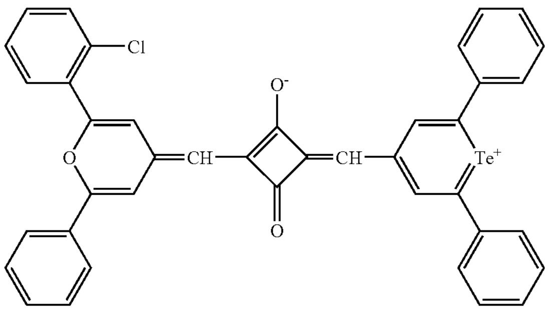

-continued
sq-53
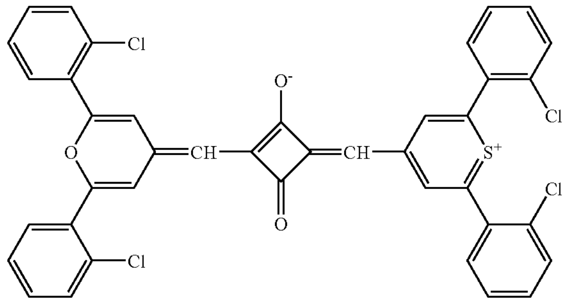
sq-54
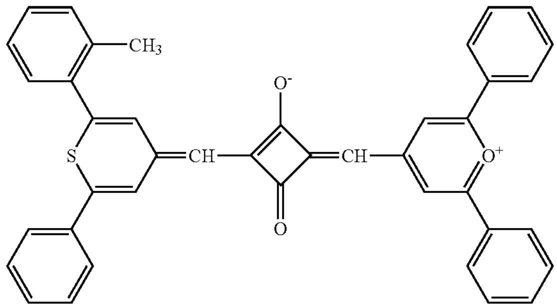
sq-55
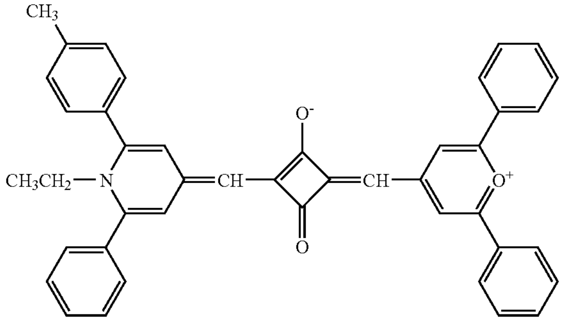
sq-56
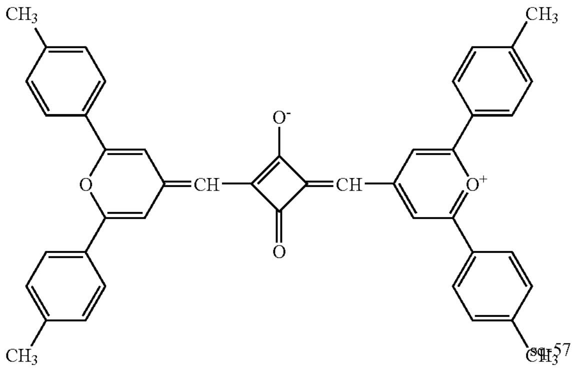
sq-57
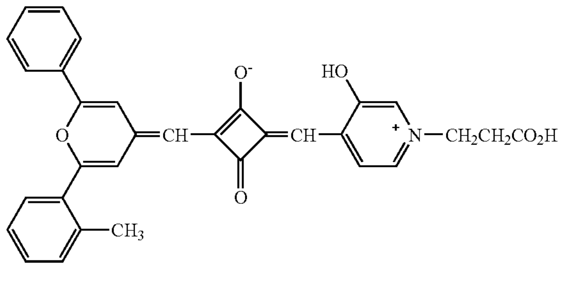
-continued
sq-58
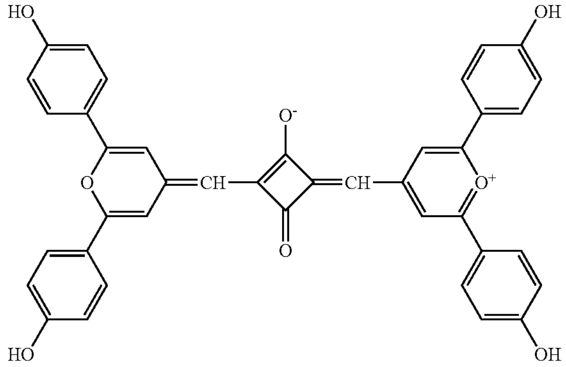
sq-59
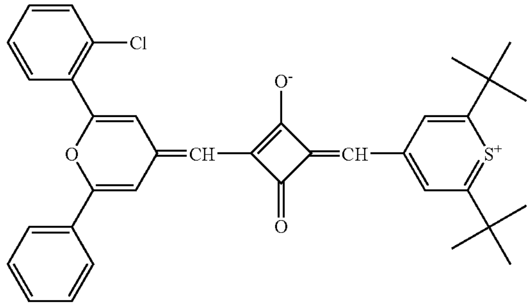
sq-60
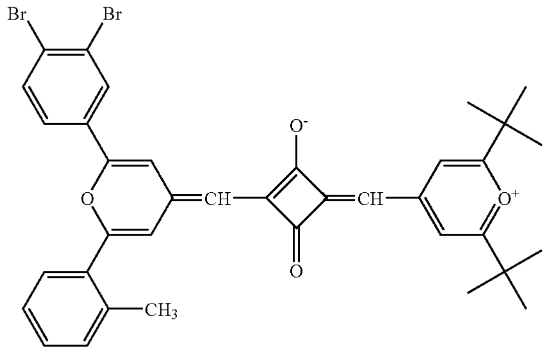
sq-61
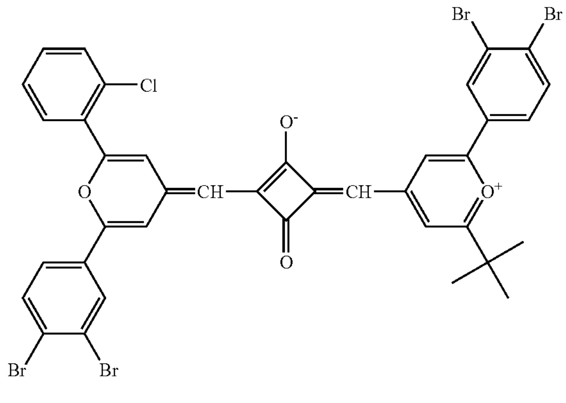

-continued
sq-62
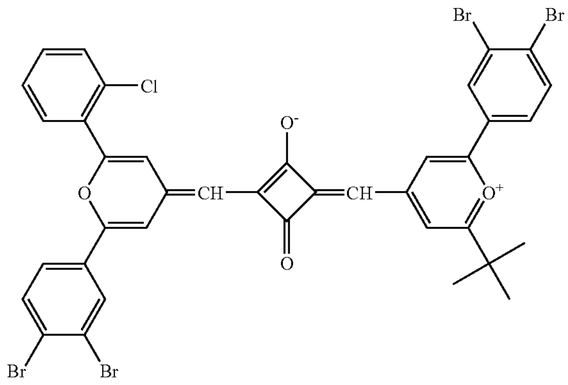
sq-63
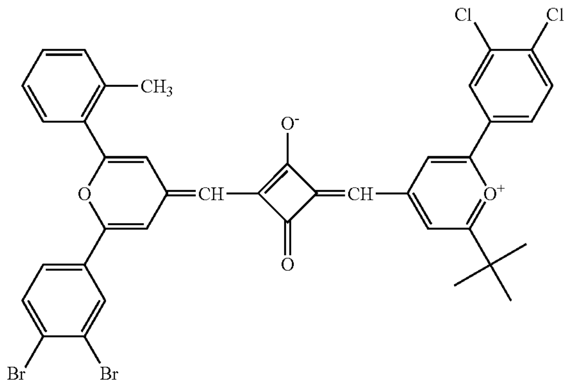
sq-64
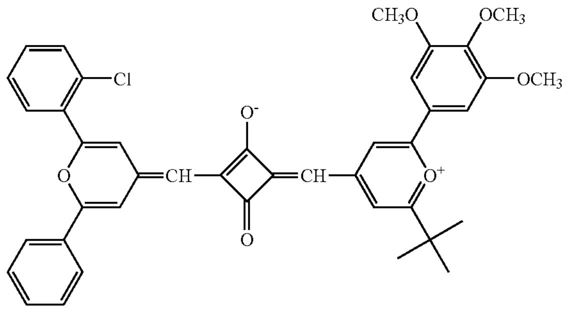
sq-65
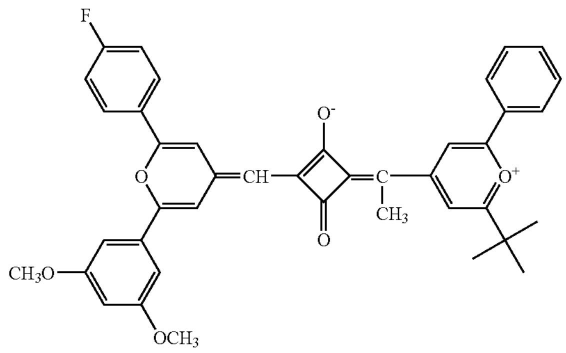
-continued
sq-66
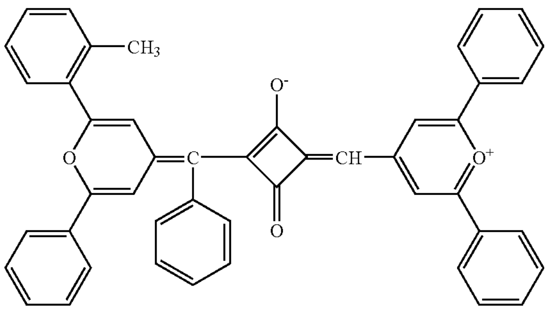
sq-67
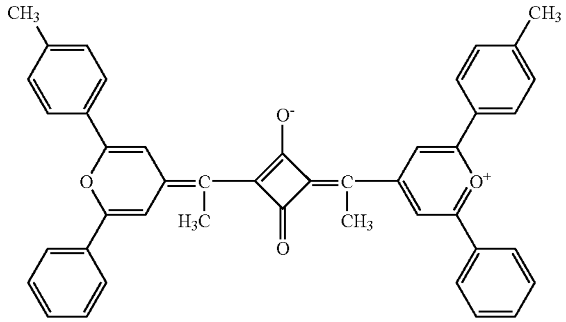
sq-68
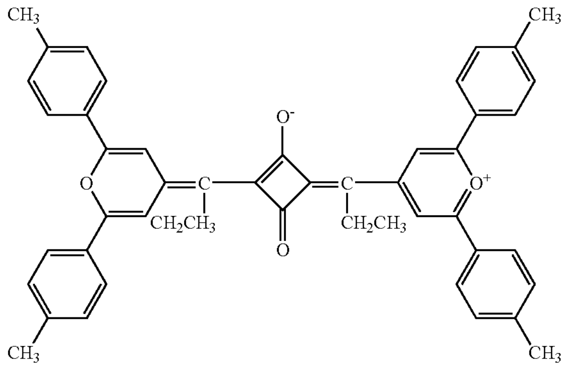
sq-69
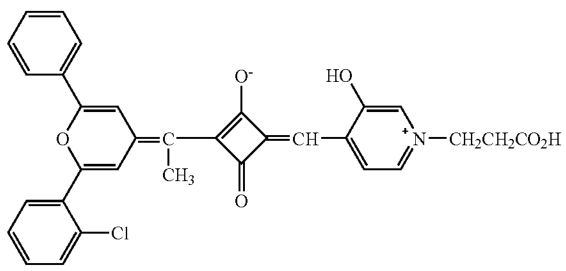

-continued
sq-70
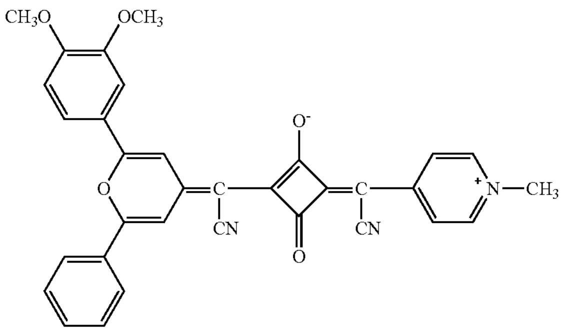
sq-71
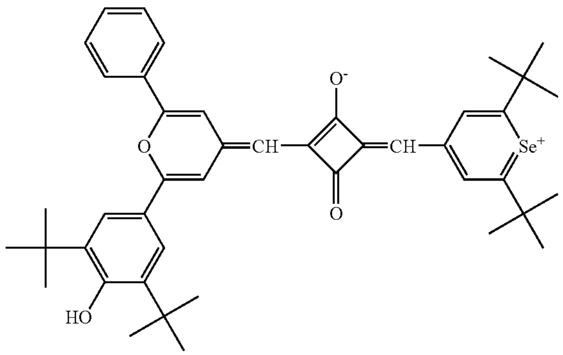
sq-72
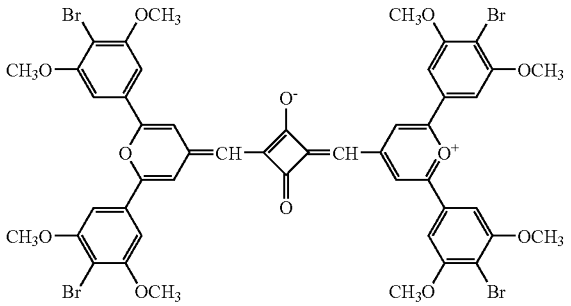
sq-73
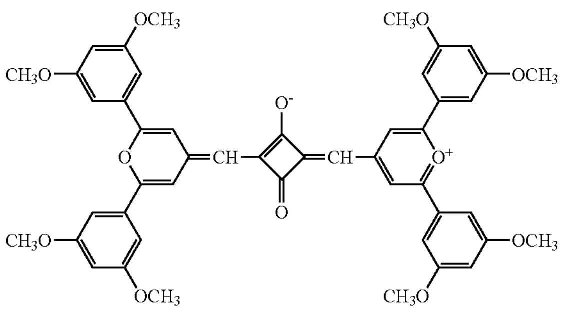
-continued
sq-74
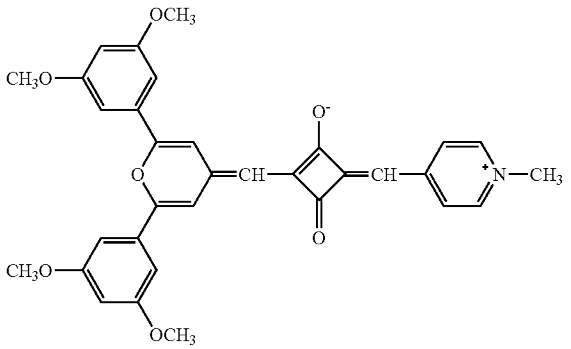
sq-75
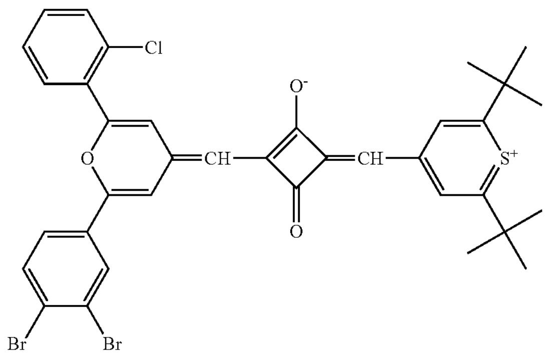
sq-76
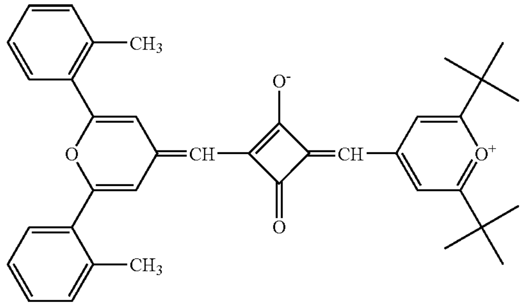
sq-77
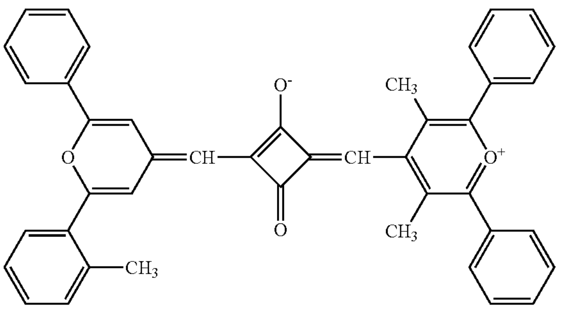

-continued
sq-78
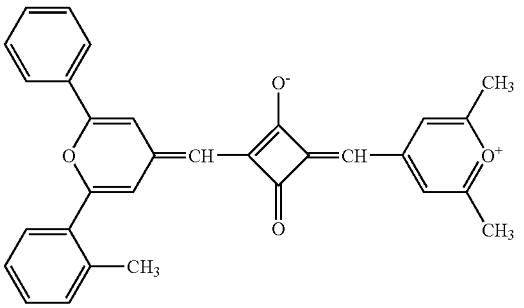
sq-79
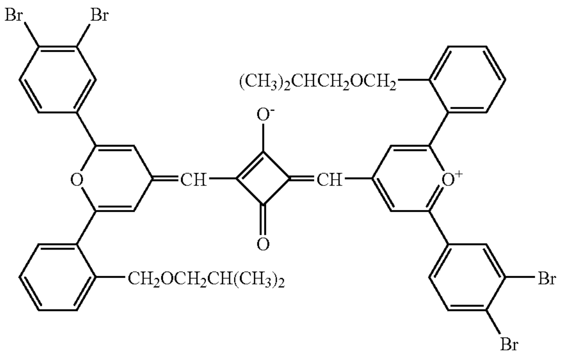
sq-80
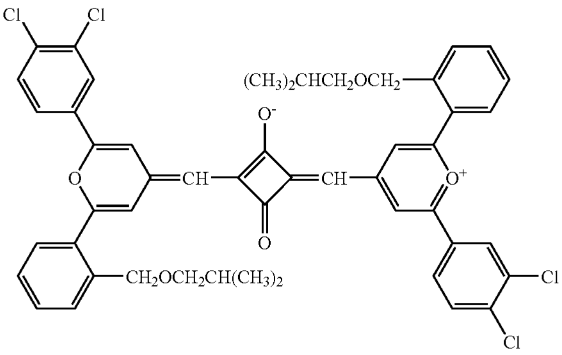
sq-81
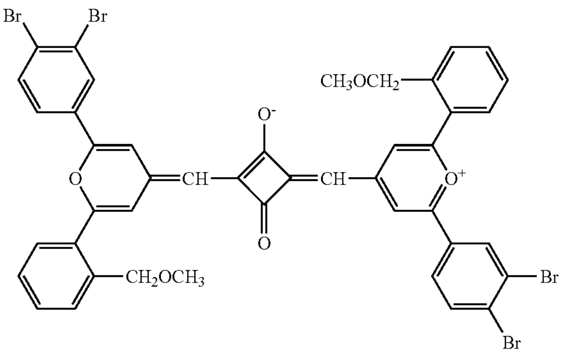
-continued
sq-82
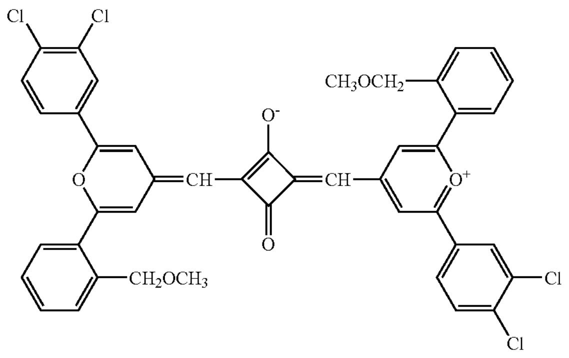
sq-83
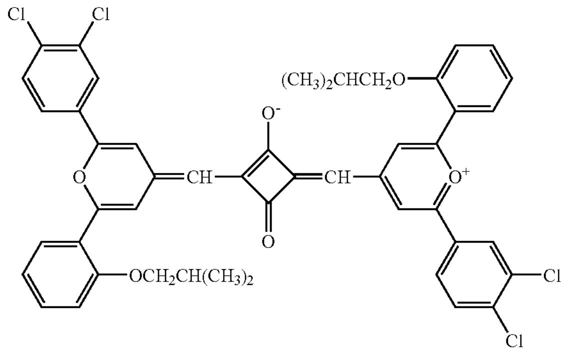
sq-84
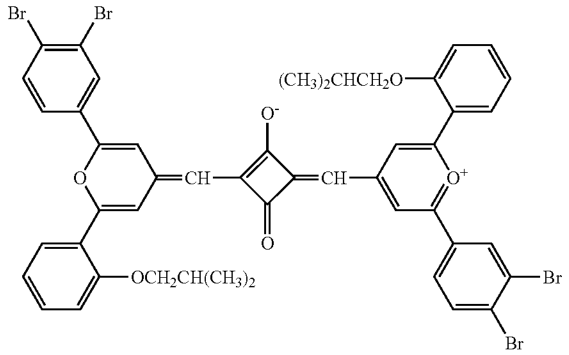
sq-85
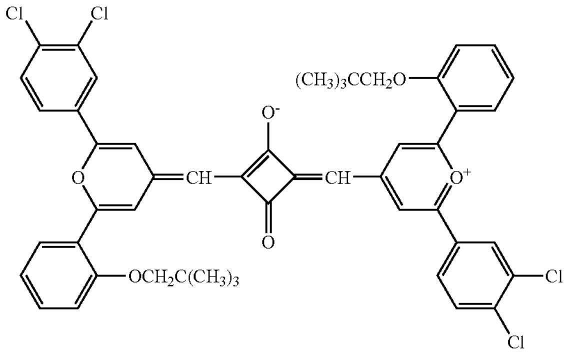

-continued sq-86

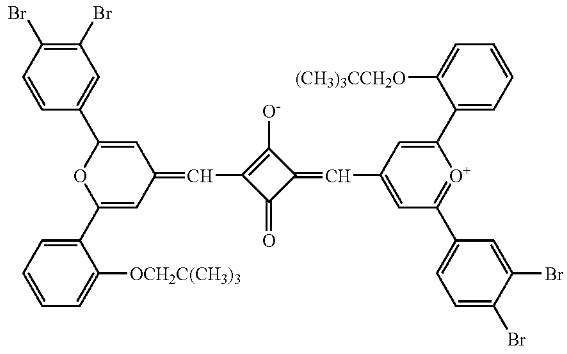

sq-87

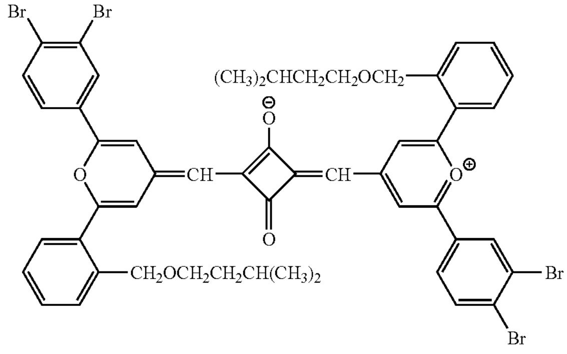

sq-88

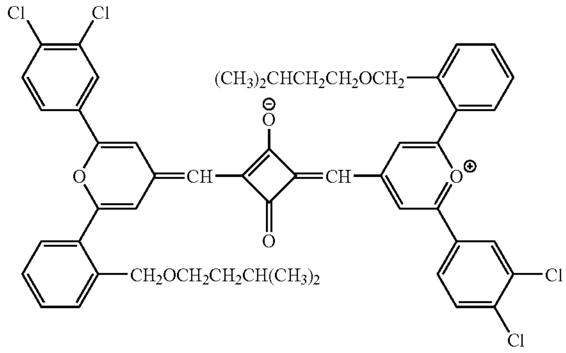

The above-described example compounds can be readily synthesized according to a method described in such as Dyes & Pigments (pp. 85–107, September, 1988), and in JP-A Nos. 10-036695, 10-158253, 2001-117201 and 2001-011070. In the following, a part of the synthesis method of compounds represented by Formulas (1)–(6) will be shown.

(Synthesis Route of Example Compound sq-38)

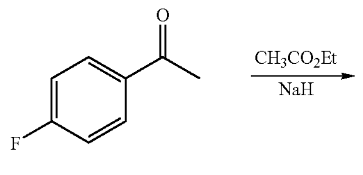

-continued

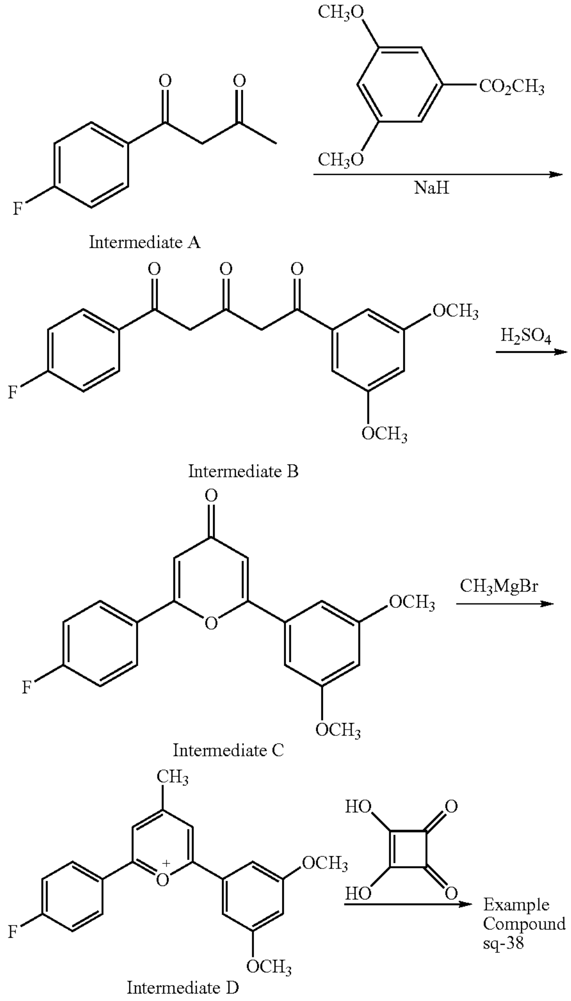

Synthesis of Intermediate A

Sodium hydride of 16.0 g was added to 50 ml of ethyleneglycol dimethylether and heated to 50° C. Into the reaction solution, a mixed solution of 27.6 g of p-fluoroacetophenone and 35.2 g of ethyl acetate was titrated, after which the solution was stirred for 5 hours while maintained at 50° C. After the reaction solution was cooled with iced water, 30 ml of methanol and 150 ml of ice and water were added in succession. Concentrated hydrochloric acid of 30 ml was added to the system, and extraction by use of 200 ml of ethyl acetate was performed, after which the extract was dried with sodium sulfate. After having been filtered under reduced pressure, the solvents were evaporated away by means of concentration under reduced pressure. The residue was purified by silica gel chromatography, whereby 17.1 g of Intermediate A was obtained.

Synthesis of Intermediate B

Combined were 19.0 g of sodium hydride and 200 ml of ethyleneglycol dimethylether and subjected to heat refluxing.

While being heat refluxed, titrated into the reaction solution over 30 minutes was a mixed solution of 17.1 g of intermediate A, 28.0 g of 3,5-dimethoxy methylbenzoate and 200 ml of ethyleneglycol dimethylether. After titration, followed by heat refluxing for 4 hours, 350 ml of ethyleneglycol dimethylether were evaporated away. The reaction solution, after having been left to cool to room temperature, was further cooled with water and 30 ml of methanol were gradually added. The reaction solution was cooled with iced water, and further added thereto was 1 L of water and 40 ml of concentrated hydrochloric acid. The system was subjected to extraction with 150 ml of ethyl acetate, and the extract was dried with sodium sulfate. After the system was filtered under reduced pressure, the solvents were evaporated away by means of concentration under reduced pressure. The residue was purified by silica gel chromatography, whereby 21.3 g of Intermediate B was obtained.

Synthesis of Intermediate C

Cooled with iced water was 200 ml of concentrated sulfuric acid, and was added to Intermediate B. The reaction solution was stirred for 2 hours while cooled with iced water. The reaction solution was titrated into 2 L of water cooled with iced water, and precipitated crystals were filtered and washed with water. The crystals were subjected to recrystalization with ethyl acetate/hexane, whereby 16.1 g of Intermediate C were obtained.

Synthesis of Intermediate D

Under a nitrogen atmosphere, 5.0 g of Intermediate C was dissolved in 400 ml of tetrahydrofuran. After the reaction solution was heated to 50° C. and 27.4 ml of bromomethyl magnesium (0.84 M tetrahydrofuran solution) was titrated, reaction was allowed for 2 hours. The reaction solution was cooled with iced water, combined with 100 ml of a saturated ammonium bromide aqueous solution, and subjected to extraction with 150 ml of ethyl acetate. The extract was dried with sodium sulfate, filtered and concentrated under reduced pressure, whereby 6.2 g of Intermediate D was obtained.

Synthesis of Example Compound sq-38

The above Intermediate D was dissolved in 60 ml of n-propanol. The solution was added to 870 mg of stearic acid and stirred for 1.5 hours at 80° C. After cooling to room temperature, precipitated crystals were filtered and washed with 20 ml of n-propanol. The obtained crystals were purified with silica gel chromatography, whereby 2.2 g of example compound sq-38 was prepared $\lambda_{max}$=817 nm in 2-butanone).

The structure of the obtained compound was confirmed by NMR spectrum and mass spectrum.

Compounds represented by Formulas (1)–(6) may be incorporated in any layer of a thermally developable photographic material, preferably in a photosensitive layer, in a photo-insensitive layer on said photosensitive layer side, or in a filter layer formed on the opposite side of said photosensitive layer sandwiching a support, but more preferably in a photosensitive layer on said photosensitive layer side, and in a filter layer formed on the opposite side of said photosensitive layer sandwiching a support. The addition amount of compounds represented by Formulas (1)–(6) is preferably $1\times10^{-5}$–10 mmol, more preferably $1\times10^{-4}$–1 mmol, but most preferably $1\times10^{-3}$–$1\times10^{-1}$ mmol, per $m^2$.

Compounds represented by Formulas (1)–(6) can be incorporated employing any well-known method in the art. That is, they can be incorporated in a coating solution by dissolving in a polar solvent such as alcohols such as methanol and ethanol, ketones such as methyl ethyl ketone and acetone, dimethylsulfoxide and dimethylformamide. Further, they may be incorporated by dispersion in water or an organic solvent as micro-particles having a maximum particle size of 1 μm. With respect to micro-particle dispersion technology, various technologies are disclosed, of which any appropriate one may be employed.

Next, the thermally developable photographic material of this invention will be explained. The photosensitive layer of a thermally developable photographic material of this invention preferably contains organic silver salt and a reducing agent, in addition to photosensitive silver halide.

Organic silver salt utilized in this invention is a reducible silver source, and is an organic acid salt containing reducible silver ion. Organic acids utilized in this invention include such as aliphatic carboxylic acid, carbocyclic carboxylic acid, heterocyclic carboxylic acid and heterocyclic compounds, but specifically preferably utilized are long chain (at typically a carbon number of 10–30 but preferably 15–25) aliphatic carboxylic acid and heterocyclic carboxylic acid provided with a nitrogen-containing heterocyclic ring. Further, an organic silver salt complex, a ligand of which has a total stability constant against silver ions of 4.0–10.0, is also useful.

Examples of such organic acid silver salts are described in Research Disclosure (hereinafter, abbreviated as RD) Nos. 17029 and 29963. Among them, silver salt of fatty acid is preferably utilized and silver behenate, silver arachidate and silver stearate are specifically preferable.

The aforesaid organic silver salt compounds can be prepared by mixing a water-soluble silver compound and a compound capable of forming a complex with silver, and such methods as normal precipitation, reverse precipitation and double-jet precipitation is preferably utilized. Further, a controlled double-jet method such as described in JP-A No. 9-127643 can also be utilized.

In this invention, organic silver salt preferably has a mean grain size of not more than 1 μm and is monodispersed. "Mean particle size of organic silver salt" refers to a diameter of an assumed equivalent sphere having the same volume as the organic silver salt grain, for example, in the case of a grain of organic silver salt being a spherical or bar-shaped grain. It also refers to a diameter of an equivalent circle image having the same area as the projected area of the primary surface in the case of a tabular grain. The mean grain size is preferably 0.01–0.8 μm but more preferably 0.05–0.5 μm. Further, monodisperse means identical to the case of silver halide described later, and monodispersibility is preferably 1–30%. In this invention, organic silver salt is preferably comprised of monodispersed grains having a maximum mean grain size of not more than 1 μm, and an image exhibiting high density can be obtained by structuring this condition. Further, in organic silver salt, tabular grains preferably occupy a maximum of 60% based on the number of the total organic silver salt grains. In this invention, "tabular grain" means one provided with a ratio of a mean grain diameter to its thickness, which is also known as aspect ratio (abbreviated as AR) of maximum of 3 represented by the following equation.

$$AR = \text{mean grain diameter } (\mu m)/\text{thickness } (\mu m)$$

Such organic silver grains are preferably ground by use of such as a media homogenizer or a high pressure homogenizer after having been appropriately subjected to preliminary dispersion together with such as a binder and a surfactant. A homogenizer, which can be utilized in the preliminary dispersion described above, includes, for example, a general stirrer such as an anchor type and a propeller type, a high speed rotary centrifuge radial type stirrer (dissolver) and a high speed rotary share type stirrer.

Further, the above-described media homogenizer includes, for example, a rotary mill such as a ball mill, a planetary-ball mill and a vibration-ball mill; a bead mill such as a media stirring mill, an atliter, in addition to a basket mill. Further, as a high pressure homogenizer, utilized may, for example, be a type in which a solution collides against such as a wall and a plug, a type in which a solution is divided into plural portions, which collide with each other, and a type in which a solution is passed through a tiny orifice.

In apparatuses used at the time of dispersing organic silver grains utilized in this invention, as a material of a part against which said organic silver grains collide, preferably utilized, for example, are ceramics such as zirconia, alumina, silicon nitride and boron nitride or diamond, of which specifically preferable is zirconia.

Organic silver grains utilized in this invention preferably contain 0.01–0.5 mg of Zr but more preferably 0.01–0.3 mg of Zr, per gram of silver. It is preferred as a preparation method of organic silver grains utilized in this invention to optimize such as a binder concentration, a preliminary dispersion method, a homogenizer operating condition and homogenizing duration.

Photosensitive silver halide according to this invention is preferably provided with a small mean grain size to minimize milky whitening after image formation and to obtain excellent image quality, and the mean grain size is preferably a maximum of 0.1 μm, more preferably 0.01–0.1 μm and still more preferably 0.02–0.08 μm. "Grain size" mentioned here indicates diameter of an equivalent circle having the same area as an individual grain image which is observed through an electronmicroscope. Further, silver halide is preferably monodispersed, which term refers to dispersibility, determined by the following equation, being a maximum of 40%. It is more preferably a maximum of 30%, but still more preferably at most 20%.

Monodispersibility=[(standard deviation of grain size)/(mean grain size)]×100

The shape of photosensitive silver halide grains is not specifically limited, however, it is preferred that the occupying ratio of Miller's index [100] surface is high and the ratio is preferably a maximum of 50%, more preferably a maximum of 70%, but still more preferably a maximum of 80%. The ratio of Miller's index [100] surface can be determined according to T. Tani, J. Imaging Sci., 29, 165 (1985) which utilizes adsorption dependence of a sensitizing dye on [111] surfaces and [100] surfaces.

Further, in this invention, another preferable shape of photosensitive silver halide grains is a tabular grain, which herein refers to having an aspect ratio (r/h) of a maximum of 3, when a square root of a projected area is grain size r μm and thickness in the perpendicular direction is h μm, and a preferable aspect ratio is 3–50. Further, the tabular grain size is preferably a maximum of 0.1 μm but more preferably 0.01–0.08 μm. These tabular grains are described in U.S. Pat. Nos. 5,264,337, 5,314,798 and 5,320,958, and targeted tabular grains can be easily prepared.

The photosensitive silver halide composition is not specifically limited and may be any of silver chloride, silver chlorobromide, silver chloroiodobromide, silver bromide, silver iodobromide or silver iodide. Emulsions utilized in this invention can be prepared according to methods described in such as Chimie et Physique Photographique (published by Paul Montel, 1967), by P. Glafkides, Photographic Emulsion Chemistry (published by The Focal Press, 1966) by G. F. Duffin, and Making and Coating Photographic Emulsion (published by The Focal Press, 1964) by V. L. Zelikman et al.

Photosensitive silver halide according to this invention preferably contains a metal ion belonging to the 6th–11th groups of The Periodic Table of Elements. As above metals, preferable are W, Fe, Co, Ni, Cu, Ru, Rh, Pd, Re, Os, Ir, Pt and Au.

These metal ions may be introduced in silver halide as a form of a metal complex or a metal complex ion, of which 6-dentate metal complexes represented by the following formula are preferable.

Formula: $[ML_6]^m$ wherein, M is transition metal selected from elements of the 6th–11th groups of The Periodic Table, L is a ligand and m is 0, 1-, 2-, 3- or 4-. Specific examples of a ligand represented by L include such as each ligand of halogenide (fluoride, chloride, bromide and iodide), cyanide, cianato, thiocyanato, selenocyanato, azide and aquo; nitrosyl and thionitrosyl, but preferable is aquo, nitrosyl or thionitrosyl. In case that an aquo ligand is present, it preferably occupies one or two of the ligands. Multiple L may be identical or differ.

M is preferably rhodium (Rh), ruthenium (Ru), rhenium (Re), iridium (Ir) or osmium (Os), and examples of a transition metal complex ion containing these metals includes such as $[RhCl_6]^{-3}$, $[RhCl_5(H_2O)]^{-2}$, $[RhBr_5(NO)]^{-2}$, $[RhCl_5(NS)]^{-2}$, $[RhCl_4(NO)(CN)]^{-1}$, $[RhCl(NO)(CN)_4]^{-2}$, $[ReCl_6]^{-3}$, $[ReBr_6]^{-3}$, $[ReCl_5(NO)]^{-2}$, $[Re(NS)Br_5]^{-2}$, $[Re(NO)(CN)_5]^{-2}$, $[RuCl_6]^{-3}$, $[RuCl_4(H_2O)_2]^{-1}$, $[RuCl_5(NO)]^{-2}$, $[ReBr_5(NS)]^{-2}$, $[RuCl_5(NS)]^{-2}$, $[OsCl_6]^{-3}$, $[OsCl_5(NO)]^{-2}$, $[Os(NO)(CN)_5]^{-2}$, $[Os(NO)(CN)]^{-1}$, $[Os(NS)Br_5]^{-2}$, $[IrCl_6]^{-3}$, $[IrCl_5(H_2O)]^{-2}$, $[IrBr_5(NO)]^{-2}$ and $[IrCl_5(NS)]^{-2}$.

The aforesaid metal ions, metal complexes or metal complex ions may be utilized alone or in combination of the same metal or of at least two different types of metals. The content of these metal ions, metal complexes or metal complex ions is generally $1\times10^{-9}$–$1\times10^{-2}$ mol, but preferably $1\times10^{-8}$–$1\times10^{-4}$ mol, per mol of silver halide.

A compound to provide these metals is preferably incorporated in the interior of silver halide grains, added at the time of silver halide grain formation, but may be added during preparation of silver halide grains, that is at any stage before or after nuclei formation, growth, physical ripening or chemical ripening. However, they are preferably added during nuclei formation, growth or physical ripening, more preferably during nuclei formation and growth, and most preferably during nuclei formation.

Addition may be carried out in several steps by dividing the total addition amount so that uniform content in the interior of a silver halide grain can be obtained. As described in JP-A Nos. 63-29603, 2-306236, 3-167545, 4-76534, 6-110146 and 5-273683, incorporation can be also carried out to result in uniform distribution formation in the grain. It is preferable that said distribution is formed within the grain. It is possible to dissolve these metal compounds in water or in a suitable organic solvent (for example, alcohols, ethers, glycols, ketones, esters and amides), and subsequently add the resulting solution. Suitable methods are in which, for example, an aqueous metal compound powder solution or an aqueous solution in which a metal compound is dissolved along with NaCl and KCl is added into a water-soluble silver salt solution or a water-soluble halide solution; when a silver salt solution and a halide solution are simultaneously added, a metal compound is added as a third solution to form silver halide grains, while simultaneously mixing the three solutions; during grain formation, an aqueous solution comprising the necessary amount of metal compound is charged into a reaction vessel; or during silver halide precipitation, dissolution is carried out by the addition of other silver halide grains previously doped with metal ions or complex ions. However, the preferred method is one in which an aqueous metal compound powder solution is dissolved along with NaCl and KCl and is then added to the water-soluble halide solution.

When said addition is carried out on the grain surface, it is also possible to charge an aqueous solution comprising the optimal amount of a metal compound into a reaction vessel immediately after grain formation, or during physical ripening, or at the completion thereof, or during chemical ripening.

In this invention, the photosensitive silver halide grains need not be desalted after forming grains, but when desalting is performed, said grains can be desalted by employing washing methods well known in the photographic art, such as a noodle method and a flocculation method.

The silver halide grains utilized in this invention are preferably subjected to chemical sensitization, employing methods well known in the art, such as a sulfur sensitization method, a selenium sensitization method or a tellurium sensitization method. Further, utilized can be a noble metal sensitization method employing compounds of gold, or platinum, palladium or iridium.

As a preferable compound utilized in the aforesaid sulfur sensitization, selenium sensitization and tellurium sensitization methods, any appropriate compound well known in the art may be employed, for example, compounds described in JP-A 7-128768. As a tellurium sensitizer, utilized may be such as diacyl tellurides, bis(oxycarbonyl) tellurides, bis (carbamoyl) tellurides, diacyl tellurides, bis(oxycarbonyl) ditellurides, bis(carbamoyl) ditellurides, compounds provided with a P—Te bond, tellurocarboxylates, Te-organotellurocarboxylic acid esters, di(poly)tellurides, tellurides, tellurols, telluroacetals, tellurosulfonatos, Te-containing heterocyclic compounds, tellurocarbonyl compounds, inorganic tellurium compounds or colloidal tellurium.

Utilized preferably in a noble metal sensitization method, may for example, be chloroauric acid, potassium chloroaurate, potassium aurithiocyanate, gold sulfide, gold selenide, or compounds described in such as U.S. Pat. No. 2,448,060 and British Patent No. 618,061.

Utilized in a reduction sensitization method, may for example, be stannous chloride, aminoimino methanesulfinate, hydradine derivatives, borane compounds, silane compounds and polyamine compounds, in addition to ascorbic acid and thiourea dioxide. Further, reduction sensitization can be performed by ripening a silver halide emulsion while keeping the pH at a maximum of 7 or the pAg at a maximum of 8.3. Further, reduction sensitization can be performed by introducing a single addition portion of a silver ion during grain formation.

Reducing agents employable in a thermally developable photographic material of this invention include those generally known in the art, such as phenols, polyphenols provided with at least two phenol groups, naphthols, bisnaphthols, polyhydroxybenzenes provided with at least two hydroxyl groups, polyhydroxynaphthalenes provided with at least two hydroxyl groups, ascorbic acids, 3-pyrazolidones, pyrazoline-5-ones, pyrazolines, phenylenediamines, hydroxylamines, hydroquinone monoethers, hydroxamines, hydrazines, amidoxims and N-hydroxyureas. Specifically exemplified examples are listed reducing agents specifically exemplified in U.S. Pat. Nos. 3,615,533, 3,679,426, 3,672,904, 3,751,252, 3,782,949, 3,801,321, 3,794,488, 3,893,863, 3,887,376, 3,770,448, 3,819,382, 3,773,512, 3,839,048, 3,887,378, 4,009,039 and 4,021,240; British Patent No. 1,486,148; Belgian Patent No. 786,086; JP-A Nos. 50-36143, 50-36110, 50-116023, 50-99719, 50-140113, 51-51933, 51-23721 and 52-84727; and Examined Japanese Patent Application Publication No. (hereinafter, referred to as JP-B) 51-35851, and in addition this invention can benefit from appropriately selected reducing agents from the ones described above which are well known in the art. As a selection method, it is most efficient to confirm suitability of a reducing agent by preparing a thermally developable photographic material actually containing said reducing agent to directly evaluate the photographic performance.

Among the above reducing agents, when silver aliphatic carboxylate is employed as an organic silver salt, a preferable reducing agent includes polyphenols, in which at least two phenol groups are connected via an alkylene group or sulfur, specifically polyphenols in which at least two phenol groups, at least one at a position adjacent to a hydroxyl-substituted position, which is substituted by an alkyl group (such as a methyl group, an ethyl group, a propyl group, a t-butyl group or a cyclohexyl group) or an acyl group (such as an acetyl group or a propionyl group), and which are connected via an alkylene group or sulfur; examples of such polyphenol compounds are 1,1-bis(2-hydroxy-3,5-dimethylphenyl)-3,5,5-trimethylhexane, 1,1-bis(2-hydroxy-3-t-butyl 5-methylphenyl)methane, 1,1-bis(2-hydroxy-3,5-di-t-butylphenyl)methane, (2-hydroxy-3-t-butyl-5-methylphenyl)-(2-hydroxy-5-methylphenyl)methane, 6,6'-benzylidene-bis (2,4-t-di-butylphenol), 6,6'-benzylidene-bis(2-t-di-butyl-4-methylphenol), 6,6'-benzylidene-bis(2,4-dimethylphenol), 1,1-bis(2-hydroxy-3,5-dimethylphenyl)-2-methylpropane, 1,1,5,5-tetrakis(2-hydroxy-3,5-dimethylphenyl)-2,4-ethylpentane, 2,2-bis(4-hydroxy-3,5-dimethylphenyl)propane, and 2,2-bis(4-hydroxy-3,5-di-t-butylphenyl)propane, which are described in U.S. Pat. Nos. 3,589,903, 4,021,249, British Patent No. 1,486,148, JP-A Nos. 51-51933, 50-36110, 50-116023, 52-84727 and JP-B 51-35727; bisnaphthols described in U.S. Pat. No. 3,672,904 such as 2,2'-dihydroxy-1,1'-binaphthyl, 6,6'-dibromo-2,2'-dihydroxy-1,1'-binaphthyl, 6,6'-dinitro-2,2'-dihydroxy-1,1'-binaphthyl, bis(2-hydroxy-1-naphthyl) methane, and 4,4'-dimethoxy-1,1'-dihydroxy-2,2'-binaphthyl; and further, sulfonamidophenols or sulfonamidonaphthols described in U.S. Pat. No. 3,801,321 such as 4-benzenesulfonamidophenol, 2-benzenesulfonamidophenol, 2,6-dichloro-benzenesulfonamidophenol, and 4-benzenesulfonamidonaphthol; as well as polyphenol compounds described in JP-A Nos. 2003-302723, 2003-315954 and 2004-4650, which are specifically preferable of all the polyphenol compounds listed above.

The suitable amount of a reducing agent, utilized in a thermally developable photographic material of this invention, is not constant and depends on the type of organic silver salt and a reducing agent, and other additives, however, is generally 0.05–10 mol and preferably 0.1–3 mol, per mol of organic silver salt. Further, in this range, at least two types of the above-described reducing agents may be employed. In this invention, it is preferable to add the aforesaid reducing agent to a photosensitive layer coating solution immediately before coating, which minimizes the variation of photographic performance due to aging of the photosensitive layer coating solution.

Next, to be explained will be preferable constituent elements for a thermally developable photographic material of this invention, other than the above-explained items will be explained.

A thermally developable photographic material of this invention is preferably constituted of a photosensitive layer containing such as organic silver salt, photosensitive silver halide and a reducing agent, and a protective layer which are made to accumulate on a support in this order, and appropriately provided with an intermediate layer being arranged between the support and the above-described photosensitive layer.

Further, also preferably utilized is a thermally developable photographic material, in which a backing layer is arranged on the surface opposite the photosensitive layer, which assures smooth transport and prevents blocking with a protective layer. Herein, each layer may be constituted of either one or more layer compositions, which may be the same or differ.

Further, in this invention, binder resins are preferably utilized to form each of the above-described layers. As such binder resin, transparent or translucent binder resins, which have been conventionally utilized, can be applied after appropriate selection, and such binder resin includes, for example, polyvinyl acetal type resin such as polyvinyl formal, polyvinyl acetoacetal and polyvinyl butyral; cellulose type resin such as ethyl cellulose, hydroxyethyl cellulose and acetyl butyl cellulose; styrene type resin such as polystyrene, styrene-acrylonitrile copolymer and styrene-acrylonitrile-acrylic rubber copolymer; vinyl chloride type resin such as polyvinyl chloride and chlorinated polypropyrene; polyester, polyurethane, polycarbonate, polyallylate, epoxy resin and acrylic type resin which may be utilized alone or in combinations of at least two types.

Herein, the above binder resin may be utilized in a protective layer, an intermediate layer, or a back-coat layer which is arranged when necessary, after appropriate selection unless it is detrimental to the desired effects of this invention. Further, utilized as a layer forming binder resin in an intermediate layer or in a back-coat layer, may be such as epoxy resin and acrylic resin, which are curable by actinic energy lays. In this invention, water-based binder resins listed below are also preferable.

As preferable resin, water-soluble polymer or water-dispersible hydrophobic polymer (latex) may be utilized. For example, listed are such as polyvinylidene chloride, vinylidene chloride-acrylic acid copolymer, vinylidene chloride-itaconic acid copolymer, sodium polyacrylate, polyethylene oxide, acrylic amide-acrylic ester copolymer, styrene-maleic acid anhydride copolymer, acrylonitrile-butadiene copolymer, vinyl chloride-vinyl acetate copolymer, and styrene-butadiene-acrylic acid copolymer. These constitute a water-based coating solution, forming a uniform resin film at the stage of coated film formation, after which they are dried. To utilize them, a water-based dispersion, comprised of such as organic silver salt, silver halide and a reducing agent, is mixed with these latexes to form a homogeneous dispersion, which can then be coated to form a thermally developable photosensitive layer. Drying a latex forms a uniform film by fusing particles thereof. Further, preferably utilized is polymer having a glass transition temperature of −20 to 80° C. and specifically preferably of −5 to 60° C. When the glass transition temperature is high, the temperature for thermal development rises, while when the glass transition temperature is low, fogging results easily to induce a sensitivity decrease and low contrast. Water dispersion polymer is preferably dispersed in a state of micro-particles having a mean particle size range of 0.001 μm to a few μm. Water dispersion hydrophobic polymer is known as latex, which is preferred to improve water resistance among those commonly utilized as a binder for water-based coating. The amount of latex to obtain water resistance as a binder is determined in view of coating behavior, however, is preferably 50–100%, but more preferably 80–100%, based on the ratio of latex to the total binder weight.

In this invention, as these binder resins, the solid content is preferably 0.25–10 times the amount of the coated silver amount, and, for example, the polymer coated amount is preferably 0.5–20 $g/m^2$ when the silver coated amount is 2.0 g $m^2$, more preferable however is 0.5–7 times the amount, where, for example, the polymer coated amount is preferably 1.0–14 $g/m^2$ when the silver coated amount is 2.0 $g/m^2$. When the amount of binder resin is at most 0.25 times that of the silver, silver tone may be significantly deteriorated to make the product unmarketable, while, the material may exhibit low contrast to make the product unmarketable when it is at most 10 times the amount of silver.

Further, in an image forming layer according to this invention, other than the above-described essential components and binder resins, various additives such as an antifoggant, a toning agent, a sensitizing dye and a supersensitizer being a substance to exhibit supersensitization, may be appropriately incorporated.

In this invention, examples of an antifoggant utilized after appropriate selection can be compounds disclosed in U.S. Pat. Nos. 3,874,946 and 4,756,999, which are heterocyclic compounds provided with at least one substituent represented by —$C(X_1)(X_2)(X_3)$ (wherein, $X_1$ and $X_2$ represent a halogen atom and $X_3$ represents a hydrogen or a halogen atom); as well as compounds disclosed in such as JP-A Nos. 9-288328 and 9-90550, U.S. Pat. No. 5,028,523, and European Patent Nos. 600,587, 605,981 and 631,176.

A toning agent which is added to improve silver tone after development includes, for example, imides (such as phthalimide); cyclic imides, pyrazoline-5-ones and quinazoline (such as succinimide, 3-phenyl-2-pyrazoline-5-one, 1-phenylurazol, quinazoline and 2,4-thiazolidinedione); naphthalimides (such as N-hydroxy-1,8-naphthalimide); cobalt complexes (such as cobalt hexamine trifluoroacetate); mercaptans (such as 3-mercapto-1,2,4-triazole); N-(aminomethyl)aryldicarboxyimides (such as N-(dimethylaminomethyl)phthalimide); combinations of blocked pyrazoles, isothiuronium derivatives and certain types of photobleaching agents (such as a combination of N,N'-hexamethylene (1-carbamoyl-3,5-dimethylpyrazole), 1,8-(3,6-dioxaoctane) bis(isothiuronium trifluoroacetate) and 2-(tribromomethylsulfonyl)bezothiazole); merocyanine dyes (such as 3-ethyl-5-{[3-ethyl-2-benzothiazolinylidene(benzothiazolinylidene)]-1-methylethylidene}-2-thio-2,4-oxazolydinedione; phthalazinone, phthalazinone derivatives and metal salts of these derivatives [such as 4-(1-naphthyl) phthalazinone, 6-chlorophthalazinone, 5,7-dimethyloxyphthalazinone and 2,3-dihydro-1,4-phthalazinedione]; combinations of phthalazinone and sulfinic acid derivatives (such as 6-chlorophthalazinone+sodium benzenesulfinate or 8-methylphthalazinone+sodium p-trisulfonate); combinations of phthalazine+phthalic acid; a combination of phthalazine (including an adduct of phthalazine) and compounds selected from maleic anhydride, and at least one compound selected from phthalic acid, 2,3-naphthalene dicarboxylic acid or o-phenylenic acid derivatives, and an anhydride thereof (such as phthalic acid, 4-methylphthalic acid, 4-nitrophthalic acid and tetrachlorophthalic acid anhydride); quinazolinediones, benzoxazine and naphthoxazine derivatives; benzoxazine-2,4-diones (such as 1,3-benzoxazine-2,4-dione); pyrimidines and asymmetric-triazines (such as 2,4-dihydroxypyrimidine), and tetraazapentalene derivatives (such as 3,6-dimercapto-1,4-diphenyl-1H, 4H-2, 3a, 5,6a-tetraazapentalene), of which preferred toning agents are phthalazone and phthalazine. Herein, a toning agent may be added in a protective layer described below, provided that the addition amount does adversely affect the desired object of this invention.

Further, as a sensitizing dye, for example, advantageous selected are simple merocyanines described in such as JP-A Nos. 60-162247 and 2-48635, U.S. Pat. No. 2,161,331, German Patent 936,071 and JP-A 5-11389 for an argon ion laser light source; tri-nucleus cyanine dyes described in such as JP-A Nos. 50-62425, 54-18726 and 59-102229, and merocyanines described in JP-A 7-287338, for a helium neon laser light source; thiacarbocyanines described in JP-B Nos. 48-42172, 51-9609 and 55-39818, as well as JP-A Nos. 62-284343 and 2-105135; tricarbocyanines described in JP-A Nos. 59-191032 and 60-80841, and for an infrared semiconductor laser light source, dicarbocyanines provided with a 4-quinoline nucleus described in Formulas (IIIa) and (IIIb) of JP-A Nos. 59-192242 and 3-67242. Further, to correspond to lasers having a wavelength region of not shorter than 750 nm and more preferably 800 nm, preferably utilized are sensitizing dyes described in such as JP-A Nos. 4-182639 and 5-341432, JP-B Nos. 6-52387 and 3-10931, U.S. Pat. No. 5,441,866 and JP-A No. 7-138295.

Further, as a supersensitizer, utilized after appropriate selection may be compounds described in RD No. 17643, JP-B Nos. 9-25500 and 43-4933, JP-A Nos. 59-19032, 59-192242 and 5-341432; and in this invention, also utilized may be heteroaromatic mercapto compounds represented by following Formula (M) and disulfide compounds represented by Formula (Ma) which generate the essential aforesaid mercapto compounds.

Ar—SM Formula (M):

Ar—S—S—Ar Formula (Ma):

In Formula (M), M is a hydrogen atom or an alkali metal atom, Ar is a heteroaromatic ring or a condensed heteroaromatic ring provided with at least one nitrogen, sulfur, oxygen, selenium or tellurium atom. The heteroaromatic ring is preferably benzimidazole, naphthoimidazole, benzothiazole, naphthothiazole, benzoxazole, naphthoxazole, benzoselenazole, benzotellurazole, imidazole, oxazole, pyrazole, triazole, triazine, pyrimidine, pyridazine, pyrazine, pyridine, purine, quinoline or quinazoline. Further, in Formula (Ma), Ar is identical to the case of above Formula (M).

The above-described heteroaromatic ring may be provided with a substituent selected from a group comprising a halogen atom (such as Cl, Br and I), a hydroxyl group, an amino group, a carboxyl group, an alkyl group (such as those having at least one carbon atom but preferably 1–4 carbon atoms) and an alkoxy group (such as those also having at least one carbon atom, but preferably 1–4 carbon atoms).

The supersensitizer utilized in this invention is preferably incorporated in the range of 0.001–1.0 mol, but more preferably in the range of 0.01–0.5 mol, per mol of silver in an emulsion layer containing organic silver salt and silver halide grains.

In the image recording layer according to this invention, a large ring compound containing a hetero atom may be incorporated. A large ring compound comprising at least a 9-membered ring containing as a hetero atom at least one type of a nitrogen atom, an oxygen atom, a sulfur atom or a selenium atom is preferable, but more preferable is a 12–24-membered ring, while most preferable is a 15–21-membered ring.

A typical large ring compound is crown ether, described below which was synthesized by Pederson in 1967, and many others have been synthesized since that unique report. These compounds are described in such as C. J. Pederson, Journal of American Chemical Society, vol. 86 (2495), 7017–7036 (1967); and G. W. Gokel, S. H. Korzeniowski, “Macrocyclic polyether synthesis”, Springer-Vergal (1982).

In a photosensitive layer according to this invention, in addition to the above-described additives, preferably utilized may be such as a surfactant, an antioxidant, a stabilizer, a plastisizer, an ultraviolet absorbent agent and a coating aid. Preferably utilized as these additives and other additives described above, are compounds described in RD Item 17029 (p. 9–15, June 1978).

In this invention, a photosensitive layer may be constituted of either a single layer or plural layers, compositions of which are the same or differ. Herein, the thickness of a photosensitive layer is generally 10–30 μm.

Next, a support and a protective layer, which are essential as constituent layers of the thermally developable photographic material of this invention, will be detailed.

A support utilized in a thermally developable photographic material of this invention includes, for example, each resin film of such as acrylic ester, methacrylic ester, polyethylene terephthalate, polybutylene terephthalate, polyethylene naphthalate, polycarbonate, polyallylate, polyvinyl chloride, polyethylene, polypropylene, polystyrene, nylon, aromatic polyamide, polyether, polyether ketone, polysulfone, polyimide, polyetherimide and triacetyl cellulose, and further resin film comprising at least two layers of the above-described resins may be accumulated.

A support according to this invention is preferably one stretched and heat-set in film form with respect to dimensional stability since the support is subjected to development by heat after latent image formation in an image recording method, to be described later. Herein, to the support may be added a filler such as titanium oxide, zinc oxide, barium sulfate and calcium carbonate, at an amount in the range to not produce adverse effects in this invention. Herein, thickness of a support is commonly 10–500 μm, but preferably 25–250 μm.

For a protective layer utilized in a thermally developable photographic material of this invention, binder resin described in the above photosensitive layer may be appropriately selected and utilized.

As additives incorporated in a protective layer, filler is preferably contained to prevent image abrasion after thermal development and to assure smooth transport, and the addition amount, if filler is added to form the protective layer, is 0.05–30 weight % of the composition.

Further, to improve a sliding property and the lubrication property, a lubricant or an antistatic agent may be incorporated in the protective layer. Such a lubricant includes, for example, fatty acid, fatty acid ester, fatty acid amide, polyoxyethylene, polyoxypropylene, (modified) silicone oil, (modified) silicone resin, fluorine-containing resin, fluoride resin, fluorinated carbon, and wax. Further, an antistatic agent includes such as a cationic surfactant, an anionic surfactant, a nonionic surfactant, a polymer antistatic agent, metal oxide or a conductive polymer; compounds described in “Chemical Products of 11290”, Kagaku Kogyo Nippoh Co., Ltd., p 875–876, and compounds described in columns 14–20 of U.S. Pat. No. 5,244,773. Various additives incorporated in a photosensitive layer may be added also in a protective layer in a range which aids in reaching the object of this invention, and the addition amount therefore is preferably 0.01–20 weight %, but more preferably 0.05–10 weight %, based on the components which form the protective layer.

In this invention, a protective layer may be constituted of either a single layer or a plural-layer composition, which may be the same or differ. Herein, the thickness of a protective layer is generally 1.0–5.0 μm.

In this invention, other than the aforesaid photosensitive layer, provided may be a support and protective layer, an intermediate layer to improve adhesion between the support and the photosensitive layer, and a back-coat layer to improve smooth transport and antistatic properties, further when these are provided, the thickness of an intermediate layer is generally 0.05–2.0 μm and the thickness of a back-coating layer is generally 0.1–10 μm.

A photosensitive layer coating solution, a protective layer coating solution, and each coating solution of an intermediate layer and a backing layer which may be provided as appropriate, may be prepared by dissolving or dispersing each aforesaid component in an appropriate solvent.

As a solvent utilized in the above preparation, those having a solubility parameter, which is shown in "Pocket Handbook of Solvent" edited by the Society of Organic Synthetic Chemistry, in a range of 6.0–15.0 can be employed, and a solvent utilizable in a coating solution to form each layer according to this invention includes, ketones such as acetone, isophorone, ethyl amyl ketone, methyl ethyl ketone and methyl isobutyl ketone; alcohols such as methyl alcohol, ethyl alcohol, n-propyl alcohol, isopropyl alcohol, n-butyl alcohol, isobutyl alcohol, diacetone alcohol, cyclohexanol and benzyl alcohol; glycols such as ethylene glycol, diethylene glycol, triethylene glycol, propylene glycol and hexylene glycol; ether alcohols such as ethylene glycol monomethylether and diethylene glycol monoethylether; ethers such as ethyl ether, dioxane and isopropyl ether; esters such as ethyl acetate, butyl acetate, amyl acetate and isopropyl acetate; hydrocarbons such as n-pentane, n-hexane, n-heptane, cyclohexane, benzene, toluene and xylene; and chlorides such as methyl chloride, methylene chloride, chloroform and dichlorobenzene; however, the solutions are not limited thereto unless adverse results counter the desired effects.

Further, these solvents can be utilized alone or in combination of a few types. Herein, the residual amount of the above-listed solvents in a thermally developable photographic material can be controlled by appropriately setting such as the temperature condition of the drying process after coating, in which the residual solvent amount is preferably 5–1000 $mg/m^2$, but more preferably 10–300 $mg/m^2$, based on the total amount.

When dispersion is conducted at the time of preparation of a coating solution, conventional homogenizers, well known in the art, such as a two-roll mill, a three-roll mill, a ball mill, a pebble mill, a coball mill, a trommel, a sand mill, a sand grinder, a Sqegvari atliter, a high-speed impeller homogenizer, a high-speed stone mill, a high-speed impact mill, a disperser, a high-speed mixer, a homogenizer, an ultrasonic homogenizer, an open kneader and a continuous kneader can be employed after appropriate evaluation.

To coat the coating solution having been prepared in the above manner, various commonly known types of coater stations such as an extrusion coater of an extrusion type, a reverse roll coater, a gravure roll coater, an air-doctor blade coater, a blade coater, an air-knife coater, a squeeze coater, an immersion coater, a bar coater, a transfer roll coater, a "kiss" coater, a casting coater and a spray coater can be preferably utilized after appropriate evaluation. Among these coaters, an extrusion coater of an extrusion type and a roll coater such as a reverse roll coater are preferably utilized, which tend to assure uniform thickness of the formed layer.

Further, at the time of forming a protective layer, a coater is not specifically limited provided that said coater does not cause damage of the photosensitive layer, however, when there is a possibility that a solvent, utilized in a protective layer coating solution, may dissolve the photosensitive layer, an extrusion coater, a gravure roll coater, and a bar coater, of the above coaters may be employed instead. Herein, among them, when a method such as a gravure roll coater and a bar coater, which contact the web to be coated, is employed, the rotation direction of the gravure roll or bar may be either forward or reverse, and the speed of forward rotation may be either same as or different from the web transport speed.

Further, in the case of each layer being applied on a previous coat, coating and drying may be repeated for each layer, however, each layer may also be simultaneously multi-layer coated and dried by a wet-on-wet method. In such case, coating can be performed by a combination of an extrusion coater of an extrusion type, and of such as a reverse roll coater, a gravure roll coater, an air-doctor blade coater, a blade coater, an air-knife coater, a squeeze coater, an immersion coater, a transfer roll coater, a "kiss" coater, a casting coater and a spray coater, and since the upper layer is coated while the lower layer is still in a wet state in such a multi-layer coating by a wet-on-wet method, adhesion between upper and lower layers will be improved.

Further, after at least a photosensitive layer coating solution having been coated in this invention, the temperature to dry the coated layer is preferably in the range of 65–100° C. to effectively achieve the desired effects of this invention. When the drying temperature is less than 65° C., variation of sensitivity due to aging may result because of insufficient reaction, while when the drying temperature is more than 100° C., fogging (coloring) may be generated in a thermally developable photographic material just after production. Further, drying duration is not specifically defined and depends on air volume during drying, however, it is preferably in the range of 2–30 minutes.

Herein, the above stated drying temperature range may be applied immediately after coating, however, it is also preferable to employ a temperature lower than 65° C. for initial drying and then apply the above temperature range, to prevent a marangoni effect of the coated solution caused during drying, as well as unevenness (the orange peel effect) due to early drying of the surface portion of the layer caused by hot blown air.

In the above-described manner, the targeted object of this invention can be achieved by a thermally developable photographic material and a suitable manufacturing method thereof; however, a sharp image without interference fringes can be obtained by further optimizing the image recording method.

Next, an image recording method suitable for a thermally developable photographic material of this invention will be detailed.

An image recording method which can be utilized in this invention is classified roughly into three embodiments based on the angle between the exposure plane and laser light, the wavelength of the laser, and the number of lasers utilized, which may be employed alone or in combination of at least two types. A sharp image without interference fringes can be obtained by such an image recording method.

In this invention, a preferable embodiment of an image recording method includes image formation by scanning exposure employing laser light in which the angle between an exposure plane of a thermally developable photographic material and the laser light never becomes perpendicular. In this manner, by shifting the incident angle from perpendicular, since the difference of light paths to reach the photosensitive layer become large, even when reflective light generated at an interlayer interface, scattering and decay on the laser light path may be generated to barely generate interference fringes. Herein, "never become perpendicular" means that the angle nearest to perpendicular during laser scanning is preferably 55–88 degrees, more preferably 60–86 degrees, but most preferably 65–84 degrees.

Further, a more preferable embodiment of an image recording method of this invention includes image formation by scanning exposure employing a vertical multi-laser in which the exposure is not a single wavwlength. When scanning exposure is performed by such a vertical multi-laser light having a specific width of wavelength, generation of interference fringes is reduced compared to scanning laser light of a single vertical mode. Herein, "vertical multi" means that the exposure is not single a wavelength and distribution of the exposure wavelength is generally at least 5 nm but preferably at least 10 nm. The upper limit of distribution of the exposure wavelength is not specifically limited, however, it is approximately typically 60 nm.

Further, in the above-described image recording method, as a laser utilized for scanning exposure, employed after appropriate selection, depending on the desired purposes, can be a solid laser such as a ruby laser, a YAG laser, and a glass laser; a gas laser such as a He—Ne laser, an Ar laser, a Kr laser, a $CO_2$ laser, a CO laser, a He—Cd laser, a $N_2$ laser and an eximer laser; a semiconductor laser such as an InGaP laser, an AlGaAs laser, a GaAsP laser, an InGaAs laser, an InAsP laser, a $CdSnP_2$ laser and a GaSb laser; a chemical laser and a dye laser, which are well known in the art; however, in the image forming method according to Claim 7, among them, a semiconductor laser at a 600–1200 nm wavelength is specifically preferably employed from among them, with respect to maintenance and physical size of the light source.

Further, in a laser utilized for a laser imager and a laser image setter, the beam spot diameter on the exposure plane of a thermally developable photographic material, when the laser is scanned on the thermally developable photographic material, is generally in the range of 5–75 μm for the short axis and of 5–100 μm for the long axis, while the scanning rate can be set at an optimum value for each thermally developable photographic material, depending on sensitivity at the emission wavelength of a laser specific to the thermally developable photographic material, and also on the laser power.

EXAMPLES

In the following, this invention will be detailed with reference to examples, however, it is not limited thereto.

Example 1

[Preparation of Subbed Photographic Support]

(Preparation of Subbed PET Photographic Support)

Both side of biaxially stretched and thermally fixed PET film, which is available on the market, at a thickness of 175 μm, and being blue at an optical density of 0.170 (measured by a Densitometer PDA-65, manufactured by Konica Corp.) was subjected to a corona discharge treatment at 8 W/m$^2$·min; following sublayer coating solution a-1 was coated on one surface and dried so as to make a dry layer thickness of 0.8 μm, resulting in sublayer A-1; and following sublayer coating solution b-1 was coated on the opposite surface and dried so as to make a dry layer thickness of 0.8 μm, resulting in sublayer B-1.

<Sublayer Coating Solution a-1>

| | |
|---|---|
| Copolymer latex solution (at a solid content of 30%) of butyl acrylate (30 weight %), t-butyl acrylate (20 weight %), styrene (25 weight %) and 2-hydroxyethyl acrylate (25 weight %) | 270 g |
| C-1 | 0.6 g |
| Hexamethylene-1,6-bis(ethyleneurea) | 0.8 g |
| Water to make | 1.0 L |

<Sublayer Coating Solution b-1>

| | |
|---|---|
| Copolymer latex solution (solid content of 30%) of butyl acrylate (40 weight %), styrene (20 weight %) and glycidyl acrylate (40 weight %) | 270 g |
| C-1 | 0.6 g |
| Hexamethylene-1,6-bis(ethyleneurea) | 0.8 g |
| Water to make | 1.0 L |

Successively, a corona discharge treatment at 8 W/m$^2$·min was applied on the surfaces of sublayer A-1 and sublayer B-1; following upper sublayer coating solution a-2 was coated on sublayer A-1 so as to make a dry layer thickness of 0.1 μm resulting in upper sublayer A-2, and following upper sublayer coating solution b-2 was coated on sublayer B-1 so as to make a dry layer thickness of 0.8 μm resulting in upper sublayer B-2.

<Upper Sublayer Coating Solution a-2>

| | | |
|---|---|---|
| Gelatin | at a weight to make | 0.4 g/m$^2$ |
| C-1 | | 0.2 g |
| C-2 | | 0.2 g |
| C-3 | | 0.1 g |
| Silica particles (mean particle size of 3 mμ) | | 0.1 g |
| Water to make | | 1.0 L |

<Upper Sublayer Coating Solution b-2>

| | |
|---|---|
| C-4 | 60 g |
| Latex solution comprising C-5 (at a solid content of 20%) | 80 g |
| Ammonium sulfate | 0.5 g |
| C-6 | 12 g |
| Polyethylene glycol (weight average molecular weight of 600) | 6 g |
| Water to make | 1.0 L |

C-1

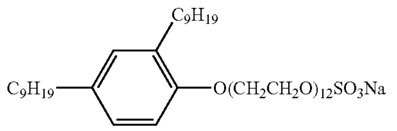

C-2

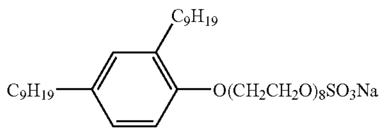

-continued

C-3

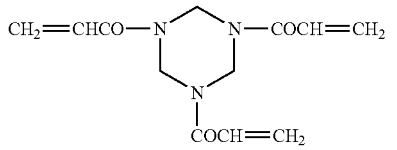

C-4

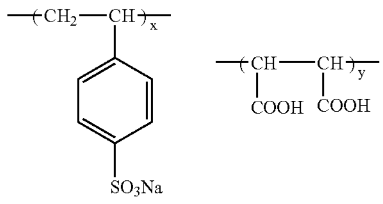

$\overline{M_n}$ = 5000

($\overline{M_n}$ is a number average molecular weight)
x:y = 75:25 (weight ratio)

C-5

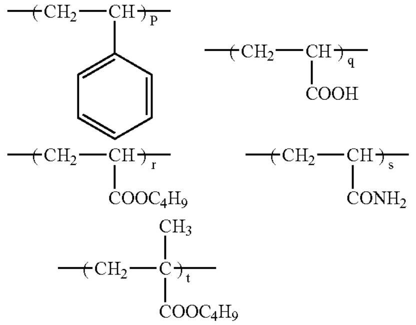

P:q:r:s:t = 40:5:10:5:40 (weight ratio)

C-6

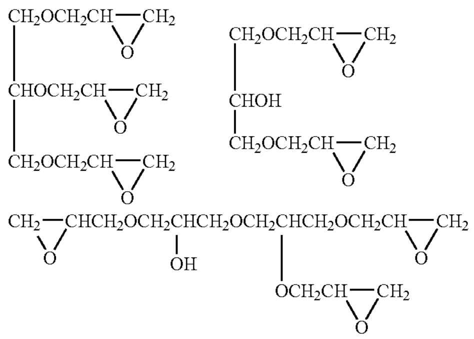

<Rear Surface Side Coating>

Into 830 g of methyl ethyl ketone while being stirred, 84.2 g of cellulose acetate butyrate (CAB 381-20, manufactured by Eastman Chemical Inc.) and 4.5 g of polyester resin (VITEL PE2200B, manufactured by Bostic Ltd.) were added and dissolved. Next, into the dissolved solution, 0.57 mmol of infrared dye (described in Table 1) was added, and further, 4.5 g of an F type surfactant (SURFLON KH40, manufactured by Asahi Glass Co., Ltd.) and 2.3 g of an F type surfactant (MEGAFAG F120K, manufactured by Dainippon Ink & Chemicals Inc.), which were dissolved in 43.2 g of methanol, were added, followed by being sufficiently stirred until dissolution. Finally, 75 g of silica, having been dispersed in methyl ethyl ketone at a concentration of 1 weight % by use of a dissolver type homogenizer, were added and stirred, whereby a coating solution for the Rear Surface Side was prepared.

The rear surface coating solution prepared in this manner was coated by use of an extrusion coater and dried so as to make a dry layer thickness of 3.5 μm. Drying was performed by use of a drying wind over 5 min. at a drying temperature of 100° C. and a dew point of 10° C.

<Preparation of Photosensitive Silver Halide Emulsion A>

| | |
|---|---|
| A1 | |
| Phenylcarbamoyl gelatin | 88.3 g |
| Compound (A) (10% methanol solution) | 10 ml |
| Potassium bromide | 0.32 g |
| Water to make | 5429 ml |
| B1 | |
| 0.67 mol/L silver nitrate aqueous solution | 2635 ml |
| C1 | |
| Potassium bromide | 51.55 g |
| Potassium iodide | 1.47 g |
| Water to make | 660 ml |
| D1 | |
| Potassium bromide | 154.9 g |
| Potassium iodide | 4.41 g |
| Iridium chloride (1% solution) | 0.93 ml |
| Water to make | 1982 ml |
| E1 | |
| 0.4 mol/L potassium bromide aqueous solution an amount to control the later mentioned silver potential | |
| F1 | |
| Potassium hydroxide | 0.71 g |
| Water to make | 20 ml |
| G1 | |
| 56% acetic acid aqueous solution | 18.0 ml |
| H1 | |
| Sodium carbonate anhydride | 1.72 g |
| Water to make | 151 ml |
| Compound (A): | |
| $HO(CH_2CH_2O)_n—(CH(CH_3)CH_2O)_{17}—(CH_2CH_2O)_mH$ | (m + n = 5 − 7) |

Employing a mixing stirrer described in JP-B Nos. 58-58288 and 58-58289, added to solution (A1) were ¼ of solution (B1) and the total solution (C1) over 4 minutes and 45 seconds utilizing a double-jet method, while adjusting the temperature to 45° C. and the pAg to 8.09, whereby nuclei were formed. After one minute, total solution (F1) was added. During mixing, the pAg was appropriately adjusted employing solution (E1). After 6 minutes, added to the resulting solution were ¾ of solution (B1) and all of solution (D1) over 14 minutes and 15 seconds employing a double-jet method, while adjusting the temperature to 45° C., and the pAg to 8.09. After said solution was stirred for 5 minutes, it was cooled to 40° C., and was added to all of solution (G1), whereby a silver halide emulsion was precipitated. The resulting supernatant was then removed while leaving 2,000 ml of resulting precipitation, to which 10 liters of water were added. After stirring, silver halide was precipitated out again. Subsequently, the resulting supernatant was removed while leaving 1,500 ml of the precipitation to which 10 liters of water were further added. After stirring, silver halide was precipitated out. After removing the supernatant while leaving 1,500 ml of resulting precipitation, solution (H1) was added and the resulting mixture was heated to 60° C. and stirred for a further 120 minutes.

Finally, the pH was adjusted to 5.8 and water was added so as to obtain a total weight of 1,161 g/mol of silver, whereby photosensitive silver halide emulsion A was prepared.

Said emulsion A was comprised of monodispersed cubic silver iodobromide grains at an average grain size of 0.058 μm, a variation coefficient of grain size of 12%, and a [100] plane ratio of 92%.

Next, the above emulsion was added with 240 ml of sulfur sensitizer S-5 (at being a 0.5% methanol solution), and further added to 1/20 mol equivalent of gold sensitizer Au-5 to said sulfur sensitizer and stirred at 55° C. for 120 minutes, whereby chemical sensitization was applied to the emulsion.

<Preparation of Powdered Organic Silver Salt A>

Dissolved in 4,720 ml of pure water at 80° C. were 130.8 g of behenic acid, 67.7 g of arachidic acid, 43.6 g of stearic acid and 2.3 g of palmitic acid. Subsequently, added to the resulting mixture were 540.2 ml of a 1.5 M sodium hydroxide aqueous solution and 6.9 ml of concentrated nitric acid, after which the resulting mixture was then cooled to 55° C., whereby a fatty acid sodium salt solution was obtained. While maintaining the temperature of said fatty acid sodium salt solution at 55° C., 45.3 g of above-described photosensitive silver halide emulsion A and 450 ml of pure water were added and stirred for 5 minutes.

Subsequently, 702.6 ml of a 1 M silver nitrate solution was added over 2 minutes and the resulting mixture was stirred for another 10 minutes, whereby an organic silver salt dispersion was prepared. Thereafter, the prepared organic silver salt dispersion was placed into a washing vessel. After adding deionized water and being stirred, the resulting dispersion was allowed to stand so that the organic silver salt dispersion was separated as the supernatant, and water soluble salts below the supernatant were removed. The supernatant organic silver salt dispersion was repeatedly washed with deionized water and drained until the electric conductivity of the drainage reached 2 μm/cm, and was then dehydrated by centrifuge. The resulting organic silver salt, in a cake form, was dried employing an air stream type flush jet dryer (produced by Seishin Kigyo Co.) under a nitrogen atmosphere, and operation conditions of controlled warm-air temperature at the dryer inlet until the water content reached 0.1%, whereby dried powdered organic silver salt A was prepared.

Herein, water content measurement of the organic silver salt composition was performed by use of an infrared water content analyzer.

<Preparation of Preliminary Dispersion A>

Dissolved in 1,457 g of methyl ethyl ketone were 14.57 g of polyvinylbutyral powder (Butvar B-79, manufactured by Monsanto Co.). Subsequently, preliminary dispersion A was prepared by gradually adding 500 g of powdered organic silver salt A while sufficiently stirring by use of a dissolver, DISPERMAT CA-40M, produced by VMA-Getzmann Co.

<Preparation of Photosensitive Emulsion Dispersion 1>

By employing a pump, preliminary dispersion A was supplied into a medium type homogenizer, Dispermat SL-C12EX Type (produced by VMA-Getzmann Co.) filled with 0.5 mm diameter zirconia beads in an amount of 80% of the interior volume, so as to obtain a retention time in the mill of 10 minutes, and was dispersed at a circumferential rate of 8 m/second, whereby a photosensitive emulsion dispersion was prepared.

<Preparation of Stabilizer Solution>

A stabilizer solution was prepared by dissolving 1.0 g of stabilizer 1 and 0.31 g of potassium acetate in 4.97 g of methanol.

<Preparation of Infrared Sensitizing Dye Solution>

An infrared sensitizing dye solution was prepared by dissolving, in a darkened place, in 31.3 ml of MEK, 19.2 mg of sensitizing dye 1, 1.488 g of 2-chloro-benzoic acid, 2.779 g of stabilizer 2 and 365 mg of 5-methyl-2-mercaptobenzimidazole.

<Preparation of Additive Solution "a">

Additive solution "a" was prepared by dissolving 27.98 g of reducing agent 1, 1.54 g of 4-methylphthalic acid and 0.92 mmol of infrared dye (described in Table 1), in 110 g of MEK.

<Preparation of Additive Solution "b">

Additive solution "b" was prepared by dissolving in 40.9 g of MEK, 3.56 g of antifoggant 2 and 3.43 g of phthalazine.

<Preparation of Photosensitive Layer Coating Solution>

Under an inert gas atmosphere (comprising 97% nitrogen gas), aforesaid photosensitive emulsion dispersion 1 (50 g) and 15.11 g of MEK were heated to 21° C. while stirring, into the mixture was added 390 μl of antifoggant 1 (at a 10% methanol solution), followed by stirring for 1 hour. Further, 494 μl of calcium bromide (at a 10% methanol solution) was added and stirred for 20 minutes. Subsequently, after 167 ml of the stabilizer solution was added and stirred for 10 minutes, 1.32 g of the aforesaid infrared sensitizing dye solution was added and stirred for 1 hour. Thereafter, the resulting mixture was cooled to 13° C. and stirred for further 30 minutes. While maintained at 13° C., 13.31 g of polyvinyl butyral (Butovar B-79, manufactured by Monsanto Co.) was added and stirred for 30 minutes, and 1.084 g of tetrachloro phthalic acid (at a 9.4 weight % MEK solution) was added and stirred for 15 minutes. Further, while stirring, 12.43 g of additive solution "a", 1.6 ml of Desmodur N3300/aliphatic isocyanate, manufactured by Mobay Co. (at a 10% MEK solution), and 4.27 g of additive solution "b" were successively added and stirred, whereby a photosensitive layer coating solution was prepared.

<Preparation of Matting Agent Dispersion>

Cellulose acetate butyrate (CAB171-15, manufactured by Eastman Chemicals, Inc.) of 7.5 g was dissolved in 42.5 g of MEK, and 5 g of calcium carbonate (Super-Pflex 200, manufactured by Speciality Minerals Co.) were added thereto. The resulting mixture was then dispersed at 8000 rpm for 30 minutes by use of a dissolver type homogenizer, whereby a matting agent dispersion was prepared.

<Preparation of Surface Protective Layer Coating Solution>

While stirring, added to and dissolved in 865 g of MEK (methyl ethyl ketone) were 96 g of cellulose acetate butyrate (CAB 171-15, manufactured by Eastman Chemicals, Inc.), 4.5 g of polymethylmethacrylic acid (Palarid A-21, manufactured by Rhom & Haas Co.), 1.5 g of a vinylsulfone compound (VSC), 1.0 G of benzotriazole, 1.0 g of a fluorine-containing surfactant (Surfron KH40, manufactured by Asahi Glass Co., Ltd.). Subsequently, 30 g of the aforesaid matting agent dispersion was added to the resulting solution, whereby a surface protection layer coating solution was prepared.

Stabilizer 1

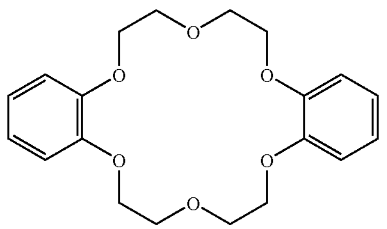

Stabilizer 2

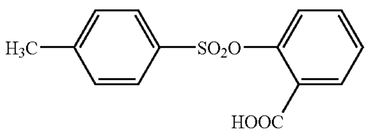

Antifoggant 1

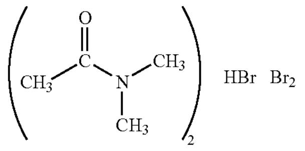

Sulfur Sensitizer S-5

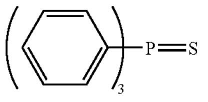

Vinylsulfone Compound (VSC)

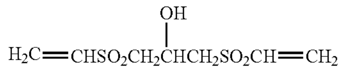

Gold Sensitizer Au-5

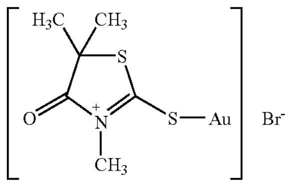

Antifoggant 2

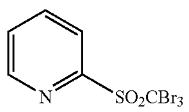

Sensitizing Dye 1

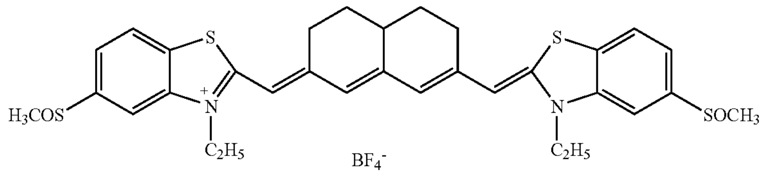

Reducing Agent 1

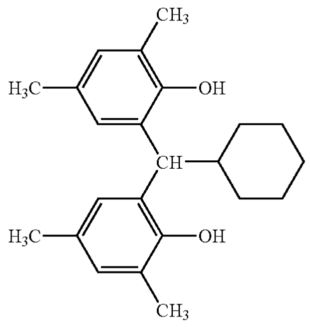

<Coating on Photosensitive Layer Side>

The aforesaid photosensitive layer coating solution and surface protective layer coating solution were simultaneously multi-coated by use of an extrusion coater to prepare a photosensitive material. Coating was performed so as to make a coated silver amount of 1.9 $g/m^2$ for a photosensitive layer and a dry layer thickness of 2.5 μm for a surface protective layer. Thereafter, drying was performed employing blown air for 10 min. at a drying temperature of 75° C. and a dew point of 10° C., whereby a coated sample (being a thermally developable photographic material) was prepared.

<Exposure and Development>

From the emulsion side of a photosensitive material prepared in the above manner, applied a laser scanning exposure by use of a semiconductor laser at a 810 nm wavelength. At this time, an image was formed by setting the angle between the exposure plane of a photosensitive material and the laser light to 75 degrees.

Subsequently, by use of an automatic processor incorporating an integral heat drum, the photosensitive material was thermally developed at 123° C. for 15 seconds, while the protective layer of said material and the drum surface were brought into contact. At that time, exposure and development were performed in a rehumidified room at 23° C. and 50% RH.

"Evaluation of Sharpness"

Three sheets of the coated samples were put into a sealed container kept at a relative humidity of 55%, followed by being forced aged at 40° C. for 20 days or at 60° C. for 7 days. With respect to the second sheet among each sample, a chest image (an image sample obtained by use of a chest phantom) was prepared, and said image was visually observed to be evaluated according to the following criteria.

A: Very sharp.

B: Good but slight blurring

C: Significant blurring to cause a slight difficulty in image reading

D: Image reading is difficult due to blurring

TABLE 1

| | Infrared Dye | | Sharpness | | |
|---|---|---|---|---|---|
| Sample No. | Backing Layer | Photosensitive Layer | 40° C., 20 days | 60° C., 7 days | Remarks |
| 1 | Comparative Dye 1 | Comparative Dye 1 | B | C | Comparison |
| 2 | Comparative Dye 2 | Comparative Dye 2 | C | C | Comparison |
| 3 | sq-1 | sq-1 | A | A | Invention |
| 4 | sq-3 | sq-3 | A | A | Invention |
| 5 | — | sq-3 | A | B | Invention |
| 6 | sq-5 | — | A | B | Invention |
| 7 | sq-13 | sq-13 | A | A | Invention |
| 8 | sq-14 | — | A | B | Invention |
| 9 | sq-15 | sq-15 | A | A | Invention |
| 10 | sq-27 | sq-27 | A | A | Invention |
| 11 | sq-37 | sq-37 | A | B | Invention |
| 12 | sq-38 | sq-38 | A | A | Invention |
| 13 | sq-73 | — | A | B | Invention |
| 14 | sq-74 | sq-74 | A | C | Invention |
| 15 | sq-75 | sq-75 | B | B | Invention |
| 16 | sq-79 | — | A | B | Invention |
| 17 | sq-79 | sq-79 | A | A | Invention |
| 18 | sq-81 | sq-81 | A | A | Invention |
| 19 | sq-84 | — | A | B | Invention |
| 20 | sq-84 | sq-84 | A | A | Invention |
| 21 | — | sq-84 | B | B | Invention |
| 22 | sq-85 | sq-85 | A | A | Invention |

Comparative Dye 1

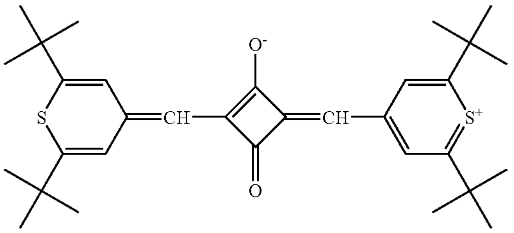

Comparative Dye 2

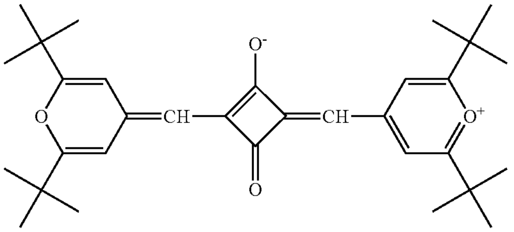

It is clear from Table 1 that samples utilizing infrared dye of this invention exhibit excellent sharpness after accelerating aging, at high temperature and high humidity, compared to comparative samples.

What is claimed is:

1. A thermally developable photographic material comprising a support, provided thereon:

(i) a photosensitive layer containing photosensitive silver halide particles, and (ii) a layer containing at least one represented by Formula (1) on one or both surfaces of the support:

Formula (1)

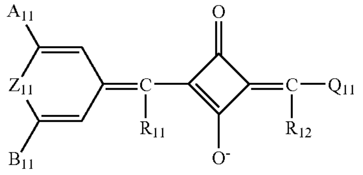

wherein, $R_{11}$ and $R_{12}$ are independently a hydrogen atom or a substituent, $Z_{11}$ is O, S, N—$R_1$, Se or Te, wherein $R_1$ is an alkyl group or an aryl group, $Q_{11}$ is a 6-membered heterocyclic ring, while $A_{11}$ and $B_{11}$ are an aryl group, and either $A_{11}$ or $B_{11}$ is a substituted aryl group.

2. The thermally developable photographic material of claim 1, wherein the compound represented by Formula (1) is further represented by Formula (2):

Formula (2)

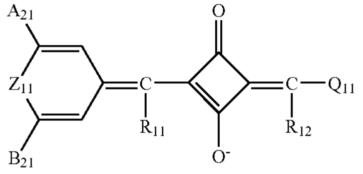

wherein, $R_{11}$, $R_{12}$, $Z_{11}$ and $Q_{11}$ are identical to $R_{11}$, $R_{12}$, $Z_{11}$ and $Q_{11}$ of Formula (1), $A_{21}$ and $B_{21}$ are also an aryl group, however $A_{21}$ and $B_{21}$ are never the same aryl group.

3. The thermally developable photographic material of claim 1, wherein the compound represented by Formula (1) is further represented by Formula (3):

Formula (3)

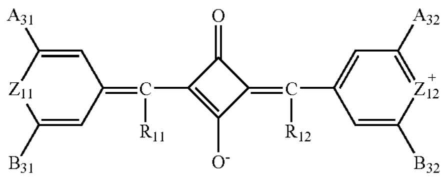

wherein, $R_{11}$, $R_{12}$ and $Z_{11}$ are identical to $R_{11}$, $R_{12}$ and $Z_{11}$ of Formula (1), $A_{31}$ and $B_{31}$ are also an aryl group, wherein at least either $A_{31}$ or $B_{31}$ is a substituted aryl group, $A_{32}$ and $B_{32}$ are also an aryl group, wherein at least either $A_{32}$ or $B_{32}$ is also a substituted aryl group, $Z_{12}$ is O, S, N—$R_2$, Se or Te, and $R_2$ is an alkyl or aryl group.

4. The thermally developable photographic material of claim 1, wherein the compound represented by Formula (3) is further represented by Formula (4):

Formula (4)

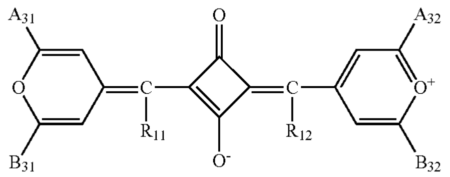

wherein, $R_{11}$ and $R_{12}$ are identical to $R_1$, and $R_{12}$ of Formula (1), also $A_{31}$, $B_{31}$, $A_{32}$ and $B_{32}$ are identical to $A_{31}$, $B_{31}$, $A_{32}$ and $B_{32}$ of Formula (3).

5. The thermally developable photographic material of claim 1, wherein the compound represented by Formula (2) is further represented by Formula (5):

Formula (5)

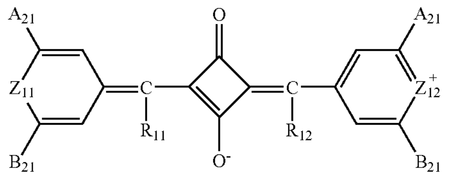

wherein, $R_{11}$, $R_{12}$ and $Z_{11}$ are identical to $R_{11}$, $R_{12}$, and $Z_{11}$ of Formula (1), $Z_{12}$ is identical to $Z_{12}$ of Formula (3), and $A_{21}$ and $B_{21}$ are the same as $A_{21}$ and $B_{21}$ of Formula (2).

6. The thermally developable photographic material of claim 1, wherein the compound represented by Formulas (4) and (5) further represented by Formula (6):

Formula (6)

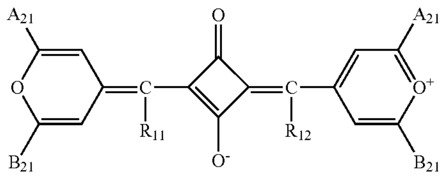

wherein $R_{11}$ and $R_{12}$ are identical to $R_{11}$ and $R_{12}$ of Formula (1), and $A_{21}$ and $B_{21}$ are identical to $A_{21}$ and $B_{21}$ of Formula (2).

7. An image forming method comprising the steps of:

(1) exposing the thermally developable photographic material of claim 1 employing a laser light source; and (2) thermally developing the exposed thermally developable photographic material at a temperature of 80 to 150° C.

8. A squalirium compound represented by Formula (6):

Formula (6)

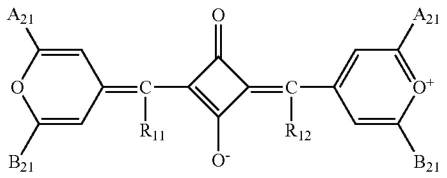

wherein $R_{11}$ and $R_{12}$ are identical to $R_{11}$ and $R_{12}$ of Formula (1), and $A_{21}$ and $B_{21}$ are identical to $A_{21}$ and $B_{21}$ of Formula (2).

* * * * *